(12) United States Patent
Jackson et al.

(10) Patent No.: US 8,652,458 B2
(45) Date of Patent: Feb. 18, 2014

(54) TISSUE GRAFT WITH NON-ALIGNED FIBER MATRIX RETAINS MESENCHYMAL PROGENITOR CELLS ON THE NON-INJURY-FACING SIDE

(75) Inventors: Wesley M. Jackson, Albany, CA (US); Leon J. Nesti, Silver Spring, MD (US); Rocky S. Tuan, Pittsburgh, PA (US)

(73) Assignees: The Henry M. Jackson Foundation for the Advancement of Military Medicine, Inc., Bethesda, MD (US); The United States of America, as represented by the Secretary of the Army, U.S.A., Washington, DC (US); The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/129,636

(22) PCT Filed: Aug. 5, 2009

(86) PCT No.: PCT/US2009/004482
§ 371 (c)(1),
(2), (4) Date: Aug. 10, 2011

(87) PCT Pub. No.: WO2010/062297
PCT Pub. Date: Jun. 3, 2010

(65) Prior Publication Data
US 2011/0318414 A1  Dec. 29, 2011

Related U.S. Application Data

(60) Provisional application No. 61/117,814, filed on Nov. 25, 2008.

(51) Int. Cl.
*A61F 2/02* (2006.01)
(52) U.S. Cl.
USPC .......................... 424/93.1; 424/484; 977/703
(58) Field of Classification Search
None
See application file for complete search history.

(56) References Cited

U.S. PATENT DOCUMENTS

| | | | |
|---|---|---|---|
| 8,216,602 B2* | 7/2012 | Ahlers et al. ................. | 424/426 |
| 2007/0041952 A1* | 2/2007 | Guilak et al. ................. | 424/93.7 |
| 2007/0269481 A1* | 11/2007 | Li et al. .......................... | 424/423 |

FOREIGN PATENT DOCUMENTS

| WO | WO 02/47557 A1 | 6/2002 |
|---|---|---|
| WO | WO 2006/138552 A2 | 12/2006 |

OTHER PUBLICATIONS

Flange Definition, The Free Dictionary.*
Hill et al. "Regulating activation of transplanted cells controls tissue regeneration." PNAS, Feb. 21, 2006, vol. 103, Isuse 8, pp. 2494-2499.*
International Search Report (PCT/ISA/210) issued on Dec. 10, 2009, by United States Patent Office as the International Searching Authority for International Application No. PCT/US2009/004482.
Written Opinion (PCT/ISA/237) issued on Dec. 10, 2009, by United States Patent Office as the International Searching Authority for International Application No. PCT/US2009/004482.
Dolores Baksh et al., "Comparison of Proliferative and Multilineage Differentiation Potential of Human Mesenchymal Stem Cells Derived From Umbilical Cord and Bone Marrow", Stem Cells, 2007, vol. 25, pp. 1384-1392.
Paolo Bianco et al., "Mesenchymal Stem Cells: Revisiting History, Concepts, and Assays", Cell Stem Cell 2, Cell Press, Apr. 2008, pp. 313-319.
Andrew C. Boquest et al., "Epigenetic Programming of Mesenchymal Stem Cells From Human Adipose Tissue", Stem Cell Reviews, vol. 2, 2006, pp. 319-329.
Edward J. Caterson et al., "Human Marrow-Derived Mesenchymal Progenitor Cells", Molecular Biotechnology, vol. 20, 2002, pp. 245-256.
Giselle Chamberlain et al., "Concise Review: Mesenchymal Stem Cells: Their Phenotype, Differentiation Capacity, Immunological Features, and Potential for Homing", Stem Cells, 2007, vol. 25, pp. 2739-2749.
M Dominici et al., "Position Paper, Minimal Criteria for Defining Multipotent Mesenchymal Stromal Cells. The International Socieity for Cellular Therapy Position Statement", Internatinal Society for Cellular Therapy, Cytotherapy, Taylor & Francis Group, 2006, vol. 8, No.4, pp. 315-317.
A Flynn et al., "Review, UC Blood-Derived Mesenchymal Stromal Cells: An Overview", International Society for Cellular Therapy, Cytotherapy, 2007, vol. 9, No. 8, pp. 717-726, Informa Healcare.
A. J. Friedenstein et al., "Osteogenesis in Transplants of Bone Marrow Cells", J. Embryol. exp. Morph., vol. 16, No. 3, pp. 581-390, Dec. 1966.
Mark Granick et al., "Toward a Common Language: Surgical Wound Bed Preparation and Debridement", Wound Repair and Regeneration, 2006, vol. 14, pp. S1-S10.
Paul Gregory et al., "The Management of Severe Fractures of the Lower Extremities", Clinical Orthopaedics and Related Research, Sep. 1995, No. 318, pp. 95-105.

(Continued)

*Primary Examiner* — Deborah Crouch
*Assistant Examiner* — Titilayo Moloye
(74) *Attorney, Agent, or Firm* — Foley & Lardner LLP

(57) ABSTRACT

A graft containing a scaffold that includes a matrix in which are positioned mesenchymal progenitor cells (MPCs) has the capacity to substantially improve wound healing, including wounds resulting from injury to nerve, bone and vascular tissue. MPCs can be harvested from debrided muscle tissue following orthopaedic trauma. The traumatized muscle-derived progenitor cells are a readily available autologous cell source that can be utilized to effect or improve wound healing in a variety of therapeutic settings and vehicles.

27 Claims, 11 Drawing Sheets

(56) References Cited

OTHER PUBLICATIONS

Wesley M. Jackson et al., "Putative Heterotopic Ossification Progenitor Cells Derived From Traumatized Muscle", Journal of Orthopaedic Research, Dec. 2009, pp. 1645-1651.

Elliot Jacob et al., "A Retrospective Analysis of Open Fratures Sustained by U.S. Military Personnel During Operation Just Cause", Military Medicine, vol. 157, Oct. 1995, pp. 552-556.

Jorma Jussila, "Measurement of Kinetic Energy Dissipation With Gelatine Fissure Formation With Special Reference to Gelatine Validation", Forensic Science International, vol. 150, 2005, pp. 53-62, Elsevier.

Jorma Jussila, "Ballistic Variables and Tissue Devitalisation in Penetrating Injury—Establishing Relationship Through Meta-Analysis of a Number of Pig Tests", Injury, Int. J. Care Injured, 2005, vol. 36, pp. 282-292.

Hideyuki Koga et al., "Synovial Stem Cells Are Regionally Specified According to Local Microenvironments After Implantation for Cartilage Regeneration", Stem Cells, Tissue-Specific Stem Cells, 2007, vol. 25, pp. 689-696.

Ken Kumagai et al., "Circulating Cells With Osteogenic Potential Are Physiologically Mobilized Into the Fracture Healing Site in the Parabiotic Mice Model", Journal of Orthopaedic Research, Feb. 2008, pp. 165-175, Wiley InterScience.

Beata Lecka-Czernick et al., "Divergent Effects of Selective Peroxisome Proliferator-Activated Receptor-γ2 Ligands on Adipocyte Versus Osteoblast Differentiation", Endocrinology, Jun. 2002, vol. 143, No. 6, pp. 1376-2384.

Steve K. Lee et al., "Peripheral Nerve Injury and Repair", Journal of the American Academy of Orthopaedic Surgeons, vol. 8, No. 4, Jul./Aug. 2000, pp. 243-252. (1-18).

George F. Muschler et al., "Selective Retention of Bone Marrow-Derived Cells to Enhance Spinal Fusion", Clinical Orthopaedics and Related Research, Mar. 2005, No. 432, pp. 242-251.

Leon J. Nesti et al., "Differentiation Potential of Multipotent Progenitor Cells Derived From War-Traumatized Muscle Tissue", Journal of Bone & Joint Surgery, vol. 90-A, No. 11, Nov. 2008, pp. 2390-2398.

Ulrich Nöth et al., "Mjltilineage Mesenchymal Differentiation Potential of Human Trabecular Bone-Derived Cells", Journal of Orthopaedic Research, vol. 20, 2002, pp. 1060-2069.

Yonggang Pang et al., "Quantitative Study of Tissue-Engineered Cartilage With Human Bone Marrow Mesenchymal Stem Cells", Arch Facial Plast Surg, vol. 7, Jan./Feb. 2005, pp. 7-11.

Bejamin K. Potter et al., "Heterotopic Ossification Following Traumatic and Combat-Related Amputations", The Journal of Bone and Joint Surgery, vol. 89-A, No. 3, Mar. 2007, pp. 476-486.

Zhuqing Qu-Petersen et al., "Identification of a Novel Population of Muscle Stem Cells in Mice: Potential for Muscle Regeneration", The Journal of Cell Biology, vol. 157, No. 5, May 27, 2002, pp. 851-864.

MK Sen et al., "Autologous ILIAC Crest Bone Graft: Should It Still Be the Gold Standard for Treating Nonunions", Injury, International Journal of the Care of the Injured, 2007, vol. 85S1, pp. S75-S80.

Anthony J. Williams et al., "Penetrating Ballistics-Like Brain Injury in the Rat: Differential Time Courses of Hemorrhage, Cell Death, Inflammation, and Remote Degeneration", Journal of Neurotrauma, vol. 23, No. 12, 2006, pp. 1828-1846.

Young-Sup Yoon et al., "Clonally Expanded Novel Multipotent Stem Cells From Human Bone Marrow Regenerate Myocardium After Myocardial Infarction", The Journal of Clinical Investigation, vol. 115, No. 2, Feb. 2005, pp. 326-338.

Cooper Jr. et al., "Encapsulated Chondrocyte Response in a Pulsatile Flow Bioreactor" Acta Biomaterialia, (2007), vol. 3, Issue 1, pp. 13-21.

Li et al., "A Three-Dimensional Nanofibrous Scaffold for Cartilage Tissue Engineering using Human Mesenchymal Stem Cells" Biomaterials, (2005), vol. 26, Issue 6, pp. 599-609.

Song et al., "Transdifferentiation Potential of Human Mesenchymal Stem Cells Derived from Bone Marrow[1]" The FASEB Journal, (2004), vol. 18, No. 9, pp. 980-982.

Song et al., "Identification and Functional Analysis of Candidate Genes Regulating Mesenchymal Stem Cell Self-Renewal and Multipotency" Stem Cells, (2006), vol. 24, No. 7, pp. 1707-1718.

Shin et al., "In vivo bone tissue engineering using mesenchymal stem cells on a novel electrospun nanofibrous scaffold," Tissue Engineering, vol. 10, No. 1-2, pp. 33-41, Jan. 2004.

Panseri et al., "Electrospun micro—and nanofiber tubes for functional nervous regeneration in sciatic nerve transections," BMC Biotechnology, vol. 8, p. 39, Apr. 11, 2008.

Zhang et al., "Bridging Small-Gap Peripheral Nerve Defects Using Biodegradeble Chitin Conduits with Cultured Schwann and Bone Marrow Stromal Cells in Rats," Journal of Reconstrutive Microsurgery, vol. 21, No. 8, pp. 565-572, Nov. 1, 2005.

Wen et al., "Effect of filament diameter and extracellular matrix molecule precoating on neurite outgrowth and Schwann cell behavior on multifilament entubulation bridging device in vitro," Journal of Biomedical Materials Research, Part A, vol. 76, No. 3, pp. 626-637, Mar. 1, 2006.

Nesti et al., "Differentiation Potential of Multipotent Progenitor Cells Derived from War-Traumatized Muscle Tissue," The Journal of Bone and Joint Surgery, vol. 90, No. 11, p. 2390, Nov. 1, 2008.

Crigler et al., "Human mesenchymal stem cell subpopulations express a variety of neuro-regulatory molecules and promote neuronal cells survival and neuritogensis", Experimental Neurology, vol. 198, No. 1, pp. 54-64, Mar. 2006.

Bulken-Hoover et al., "Inducible Expression of Neurotrophic Factors by Mesenchymal Progenitor Cells Derived from Traumatically Injured Human Muscle," Molecular Biotechnology; Part B of Applied Biochemistry and Biotechnology, vol. 51, No. 2, pp. 128-136, Sep. 9, 2011.

Supplementary European Search Report issued on Oct. 31, 2013 in application number EP 09829422.

* cited by examiner

Tube 1: a) mince source tissue into pieces and digest, e.g., with enzymes; b) incubate, e.g., at 37°C for 90 minutes Tube 2: a) shear digested tissue, and wash cells; b) collect cells, e.g., by centrifugation Culture of progenitor cells in growth medium and neurotrophic induction medium a,b,c: p<0.05, one-way ANOVA with post-hoc comparisons and n=4

Aligned Fibers (Interior core)    Random Fibers (Exterior)    Seeded with Cells

BDNF enrichment though graft:

MPCs in GM    MPCs in NM

TISSUE GRAFT WITH NON-ALIGNED FIBER MATRIX RETAINS MESENCHYMAL PROGENITOR CELLS ON THE NON-INJURY-FACING SIDE

BACKGROUND

Debridement of contaminated and devitalized tissue is the first step in the surgical treatment of open extremity injuries. This event is often part of a process comprising serial debridements over the span of several days to fully assess the viability of the remaining tissue.

Penetrating trauma results in substantial bone and soft tissue loss due to the primary injury and the debridement process. For example, as a projectile or blast wave penetrates the skin, it transfers kinetic energy to the surrounding structures, which include bone, muscle, tendon, cartilage, and fat. Jussila J. *Measurement of kinetic energy dissipation with gelatine fissure formation with special reference to gelatine validation. Forensic Sci Int* 2005, 150: 53-62. This energy is absorbed in the form of heat, mechanical stress, and chemical stress, and it initiates a number of events, including cell necrosis, apoptosis, and inflammation. *Jussila J., Forensic Sci Int.*, 150: 53-62; and Jussila J, et al, Ballistic variables and tissue devitalisation in penetrating injury—establishing relationship through meta-analysis of a number of pig tests. Injury. 2005, 36:282-92.

While much of the initial damage is largely the result of necrosis and can be seen within the first twenty-four hours, delayed tissue death can result from induced programmed cell death or vascular compromise and may not be apparent for several days after the initial event. Williams A J, et al, *Penetrating ballistic-like brain injury in the rat: differential time courses of hemorrhage, cell death, inflammation, and remote degeneration, J Neurotrauma*, 2006, 23:1828-46. Thus, the serial tissue debridement protocol is necessary to avoid premature wound closure and to minimize the amount of retained devitalized tissue.

After debridement, the tissues are reassessed and definitive treatment is planned. The degree and nature of tissue loss determine the need for tissue-grafting or tissue substitutes that are often derived from allograft or synthetic sources. After fracture fixation and closure or coverage of open wounds, revision and reconstructive surgery is frequently required to restore the function of the injured extremity. In many instances, this may require bone and soft-tissue augmentation, lysis of adhesions (about joints and along tendons), and/or ligament reconstruction. In most cases, revision surgery stems from a need to repair or replace absent, damaged, or deranged tissues such as articular cartilage, tendon, and/or bone with use of autograft, allograft, bioengineered tissue replacement, or prosthetic materials and devices. Unfortunately, these options for tissue repair or replacement are limited by the inability of the implant to fully integrate and subsequently remodel. In addition, the inferior structural, biomechanical, and biochemical properties of the implant as compared with normal human tissue prevent full restoration of the structure-function relationship.

An essential component of all tissue-engineering construct designs is a readily available, viable, and plastic cell source. Many sources of multipotent progenitor cells (e.g., bone marrow, trabecular bone, adipose tissue, umbilical cord blood, and synovial tissue), which yield cells that have varying degrees of regenerative potential and that can be expanded in vitro, have been described. Caterson E J, et al, *Human marrow-derived mesenchymal progenitor cells: isolation, culture expansion, and analysis of differentiation. Mol. Biotechnol.*, 2002, 20:245-56; Noth U, et al, *Multilineage mesenchymal differentiation potential of human trabecular bone-derived cells. J Orthop Res.*, 2002, 20:1060-9; Flynn A, et al, *UC blood-derived mesenchymal stromal cells: an overview. Cytotherapy.* 2007, 9:717-26; Boquest A C, et al, *Epigenetic programming of mesenchymal stem cells from human adipose tissue, Stem Cell Rev.*, 2006, 2:319-29; Koga H, et al, *Synovial stem cells are regionally specified according to local microenvironments after implantation for cartilage regeneration, Stem Cells,* 2007, 25:689-96. However, these tissue types may not be readily available as a source of autologous multipotent cells at the time of musculoskeletal trauma.

Adult stem cells are a useful clinical resource to enhance many healing processes. One limitation, however, is the lack of availability of one's own adult stem cells without invasive surgical procedures.

Peripheral nerve injury frequently accompanies musculoskeletal trauma, which lengthens the recovery time and leads to significant dysfunction. Current treatment of peripheral nerve injuries includes primary repair, nerve autograft, or use of synthetic nerve tubes. The success of nerve repair depends primarily on the speed of axonal growth and myelination to bridge the damaged region and decrease the time to end organ re-innervation. Lee S K, et al, *Peripheral nerve injury and repair, J Am Acad Orthop Surg.* 8, 243, 2000.

Conventional nerve tubes contain a single lumen to guide the regenerating nerve from proximal to distal stump. Although increasing the likelihood that some axons in the nerve will reconnect with the distal end, many are unable to reconnect, and gaps larger than critical size defect are likely never to regenerate.

SUMMARY OF THE INVENTION

Mesenchymal progenitor cells (MPCs) are found in traumatized tissue. MPCs share characteristic features of mesenchymal stem cells (MSCs). Nesti L J, et al. *Differentiation potential of multipotent progenitor cells derived from war-traumatized muscle, J. Bone Joint Surg. Am.*, 90, 2390-98 (2008). This and all other references cited herein are incorporated by reference.

Based upon our further observation and work with MSCs, we have discovered new methods for collecting and/or isolating MPCs from musculoskeletal wound tissue; and we have devised various therapeutic devices and methods for employing MPCs in regenerative medicine.

We present a method of harvesting mesenchymal progenitor cells (MPCs) as an alternative source of cells from debrided muscle tissue following orthopaedic trauma. MPCs offer advantages over MSCs of being more plentiful (particularly in wound tissue), more easily obtained, and capable of producing substantial quantity of various trophic factors, including neurotrophic factors, vasculotrophic factors, and osteotrophic factors. MPCs have the added advantage of diminishing inflammation and scar formation.

Also disclosed herein is a new way of using MPCs in the treatment of various tissue injury or disease states. By positioning MPCs near the injury or defect, and in fluid contact with the injury or defect, the MPCs can be used as an in situ or in vivo source of various biologically significant and therapeutically effective factors, e.g., growth factors and differentiation inducing factors that promote regeneration and/or healing. The MPCs are not consumed, nor are they completely differentiated in the process. Jackson, W. M, et al., *Putative Heterotopic Ossification Progenitor Cells Derived from Traumatized Muscle*, J. Ortho. Research, 1, (2009) (published online at www.interscience.wiley.com, DOI 10.1002/ jor.20924). Rather, they substantially remain as MPCs and continue to secrete trophic factors and promote differentiation of other cell types to regenerate the damaged tissue for a considerable time. In vitro studies show that MPCs continue to secrete trophic factors when the MPCs were at passage 2-3, which corresponds roughly to 12-15 population doublings, or approximately 3-4 weeks after harvest. MPCs likely continue to express trophic factors as long as they remain in an undifferentiatied state.

The grafts of the present invention exploit unique properties of MPCs, i.e., in a wound setting they remain in an undifferentiated state for a prolonged period, and during that time secrete trophic factors that aid in the regeneration of nerve, bone, vasculature and the like. The grafts comprise: 1) a structural element that may be referred to herein as a scaffold, and 2) a therapeutic element. The scaffold may be structured in the form of a conduit, wrap, patch, or the like. In some embodiments, the scaffold includes at least a first component that is a porous matrix. The porous matrix can be in the form of a woven or non-woven material, including natural or synthetic fibers. Among other things, the matrix serves as a reservoir or repository for a therapeutic component. As discussed more below, the scaffold may further comprise a core of aligned fibers or a conduit interior to and in fluid communication with the matrix, and/or a dam or substantially fluid impermeable sheath exterior to the matrix. The therapeutic component may include a cellular component such as MPCs. Additionally, the therapeutic component may include other therapeutic elements such as small molecule active agents commonly used to aid healing or fight infection. The matrix retains the therapeutic component such as the MPCs, but permits fluid flow within and through the matrix. The MPC-seeded matrix may be placed proximate to the injury or defect, and in fluid contact with the injury or defect.

As used herein, the term matrix is used to refer to a porous material within which MPCs, and perhaps other cells or therapeutic materials, may be infused and retained. The matrix material may be natural or synthetic, and may be additionally treated with substances to enhance retention of cells, e.g., treatment of polymeric material with hyaluronic acid. While it is desirable to retain MPCs and the like within the matrix, it is to be understood that some migration will occur, both to the interior and exterior of the various grafts. The porosity and retention capacity of the matrix can be varied according to known methods depending on the intended application, the type of graft employed, the type of tissue under treatment, and the severity of the injury or defect.

A second scaffold component may be added to the graft. One such element provides structural support for tissue regeneration and/or isolation and protection of the injury or defect. The second component can be a structural element serving as a guide or framework on which the regenerated tissue can form, or it can be a structural element that creates and/or retains a void in or around the defect, or otherwise supports and/or retains the damaged tissue as it is to be reformed so as to permit the tissue to regenerate and return to its original dimension and shape. As used herein, the term "tissue" includes nerve, bone, and vascular tissue.

These grafts may also comprise an element exterior to the matrix to isolate and/or concentrate the MPCs and the various factors produced, and to avoid loss or migration of other regenerative elements such as other cell types. The exterior element can be fabricated to match the overall structure of the scaffold, e.g., conduit, wrap, or patch. The material used in all of the foregoing elements may be the same or different, and may be fabricated to afford differing levels of porosity. The exterior element can be fabricated to be substantially or completely non-porous. The exterior element, which may function as a dam or fluid retention device to protect and isolate therapeutic components, can also be formed of biocompatible nanofibers, and created to varying levels of porosity. Thus, for example, the dam can be made substantially or entirely fluid impermeable; or it can be made to be permeable but less so than the matrix.

MPCs express neurotrophic factors (e.g., BDNF, CTNF, NT-3), which encourage axonal growth and nerve regeneration. Since nerve damage frequently occurs in orthopaedic injury, the traumatized muscle-derived progenitor cells are a readily available autologous cell source that can be utilized to effect or improve nerve repair. MPCs may be used quite effectively in a nerve graft.

We provide here a device for regenerating injured or damaged nerve, and for enhancing the rate of axonal growth. One such device incorporates a composite of nanofiber structures, and wherein the fibers are used to construct two zones or chambers within the nerve graft conduit. In the interior of the graft is a core of aligned fibers along the axis of symmetry through the longitudinal axis of symmetry of the graft. An exterior sheath surrounding the core is fabricated of randomly non-aligned fibers to serve as a matrix for seeding and supporting the MPCs, which promotes the activity of the MPCs and other endogenous neuronal support cells (e.g., Schwann Cells can migrate into the graft).

Also disclosed is a method of fabricating a novel peripheral nerve graft to include a core of aligned nanometer-scale fibers, and an outer sheath to support and retain the MPCs proximate to the wound or injury following implantation of the device. The aligned fibers guide the regeneration of individual neurons of the nerve.

In one embodiment, MPCs are loaded into a nerve graft in the form of a tissue engineered peripheral nerve conduit. One such conduit includes a porous matrix in the form of an outer sheath. MPCs are seeded within the matrix. Trophic factors produced by MPCs are secreted within close proximity of the injured nerve tissue thereby promoting healing and differentiation of other cell types to regenerate the damaged tissue. The outer sheath surrounds an interior area of the conduit. The interior area may be a void within which the nerve regeneration is afforded space to reconnect the proximal and distal ends of the nerve stub, or it may comprise a core of aligned nanometer-scale fibers that guide the regeneration of individual neurons of the nerve. The aligned fibers may be generally linear along an axis of symmetry running longitudinally through the conduit. Trophic factors produced by MPCs diffuse to the region of the aligned fibers, and promote regeneration of the nerve along those fibers.

In one embodiment of the invention, there is a nerve graft, and methods of making same, wherein the graft comprises a nerve tube having a central region or sheath filled with aligned fibers (also referred to herein as "nanofibers"). As used herein, the term nanofibers refers to fibers of about 0.05-0.5 µm in diameter; or about 0.1-0.3 µm in diameter; or 0.2 µm in diameter.

In one embodiment, the nerve tube comprises a composite of electrospun fibers, both linear (e.g., at the inner sheath) and nonlinear (e.g., at the outer sheath). The nerve tube device promotes axonal growth along the linear, aligned fibers aided by neurotrophic factors secreted by support cells seeded in the support matrix. In one embodiment, the nerve tube is fabricated by a novel two step electrospinning process. The novel electrospinning process can produce electrospun fibers on a non-conductive mandrel.

Axonal nerve tubes have previously been used to guide the regeneration of damaged nerve. Commercially available nerve tubes consist of collagen, or a similar biological or biocompatible polymer, in the shape of a hollow tube that is telescoped over the ends of the damaged nerve stumps. The limitation of these devices is related to the speed of the axonal growth through the hollow interior of the tube. If the axons do not reconnect with the distal stump within several weeks, the nerve cannot be regenerated. A device that increases rate of axonal growth will bridge longer nerve gaps during axonal growth. The devices and methods disclosed herein facilitate functional regeneration for a wide range of nerve injuries, both in terms of length of damaged nerve and in speed of regeneration.

Also disclosed herein is a method of harvesting MPCs from traumatized muscle; and isolated MPCs free of fat, fascia, bone, muscle tissue, necrotic tissue, and other cell types associated with musculoskeletal wounds. MPCs express neurotrophic factors (e.g., BDNF, CTNF, NT-3). The neurotrophic factors stimulate and promote axonal growth and nerve regeneration by increasing the rate of axonal outgrowth. Since nerve damage frequently occurs in orthopaedic injury, the traumatized muscle-derived progenitor cells are a readily available autologous cell source that improve nerve repair. This can be achieved by loading MPCs into a tissue engineered peripheral nerve conduit (nerve tube) as described elsewhere herein.

Among other things, the present invention affords means and devices for using a new cell type (MPC) found in traumatized muscle tissue. MPCs possess potent regenerative properties. They can be harvested in high numbers directly from traumatized muscle tissue, and can be employed immediately in various therapies for effecting nerve regeneration. MPCs afford an autologous resource for therapeutic material useful in various new and known therapies. By affording an autologous resource, the risk of allogenic response in a patient is dramatically reduced, if not eliminated.

BRIEF DESCRIPTION OF THE DRAWINGS

FIG. 14($a$): Electron micrographs of composite scaffold (1) interior core of aligned nanofibers, (2) surrounding non-aligned fibers, (3) non-aligned fibers seeded with MPCs; 14($b$): Viability of seeded cells in graft in GM and NM; 14($c$): BDNF production of MPCs in GM and NM; and 14($d$): Cross section of BDNF-secreting MPCs in peripheral nerve graft.

DETAILED DESCRIPTION

Figure 1:
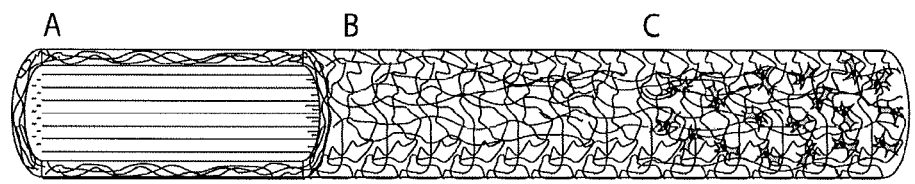
FIG. 1: Is a schematic of the peripheral nerve guide. (A) Aligned nanofibers for the core of the device guide and support the growing axons. (B) A non-aligned sheath bundles the aligned fibers and provides support for (C) mesenchymal progenitor cells, which provide biochemical factors to enhance nerve regeneration.

Debrided muscle contains multipotent cells useful in cell-based tissue-engineering therapies and studies. Following a modified stem cell isolation protocol on tissues obtained at surgery, we obtained viable cells expressing markers characteristic of mesenchymal stem cells. See, e.g., Chamberlain G, et al, *Concise review: mesenchymal stem cells: their phenotype, differentiation capacity, immunological features, and potential for homing, Stem Cells*, 2007, 25:2739-49; Baksh D, et al, *Comparison of proliferative and multilineage differentiation potential of human mesenchymal stem cells derived from umbilical cord and bone marrow, Stem Cells*, 2007, 25:1384-92. We defined these cells as mesenchymal progenitor cells, or MPCs.

These mesenchymal progenitor cells were culture-expanded, and they exhibited multipotentiality (adipogenic, osteogenic, and chondrogenic) on appropriate induction. These MPCs can be used in the initial reparative process or in future reconstructive operations in combination with appropriate tissue-engineering biomaterial scaffolds.

These studies are particularly significant in that they were performed not on animal models but human tissues and cells derived from traumatized muscle. Also, the histological evidence of differentiation was compared with differentiated bone-marrow-derived mesenchymal stem cells, a well-characterized cell type with known multiple differentiation potential. Finally, multiple assays were performed to verify the multipotent differentiation activities of the traumatized muscle-derived MPCs.

The differentiation assays were corroborated by the expression of corresponding adipogenic, osteogenic, and chondrogenic lineage-specific genes. On the basis of these findings, we have verified that muscle-derived MPCs have the potential to differentiate into osteoblasts, adipocytes, and chondrocytes.

MPCs derived from traumatized muscle require substantial characterization in terms of their origin within the body and their relationship to better-characterized stem cell types. The MPCs may originally reside in the nontraumatized muscle tissue in a quiescent state (i.e., as pericytes) (Bianco P, et al, *Mesenchymal stem cells: revisiting history, concepts, and assays*, Cell Stem Cell., 2008, 2:313-9), or they may have migrated from the bone marrow to the site of injury in response to wound-healing signals. Kumagai K, et al, *Circulating cells with osteogenic potential are physiologically mobilized into the fracture healing site in the parabiotic mice model. J Orthop Res.* 2008; 26:165-75; Friedenstein A J, et al, *Osteogenesis in transplants of bone marrow cells. J Embryol Exp Morphol.* 1966, 16:381-90.

Initial plating of the MPCs yielded a greater number of tissue-adherent cells than is typically reported for progenitor cell populations. Without being bound by any theory, this might have been due to a lower overall cellularity and a higher percentage of MPCs relative to other erythroid or mononuclear cell types in traumatized muscle compared with other sources. General characteristics of the Mesenchymal progenitor cells, such as the associated cell-surface markers, prolonged culture-expansion capabilities, and multidifferentiation potential, are characteristic features of mesenchymal stem cells. Chamberlain G, et al., *Concise review: mesenchymal stem cells: their phenotype, differentiation capacity, immunological features, and potential for homing. Stem Cells.* 2007; 25:2739-49; Dominici M, et al, *Minimal criteria for defining multipotent mesenchymal stromal cells. The International Society for Cellular Therapy position statement. Cytotherapy.* 2006; 8:315-7; Yoon Y S, et al, *Clonally expanded novel multipotent stem cells from human bone marrow regenerate myocardium after myocardial infarction. J Clin Invest.* 2005; 115:326-38; Pang Y, et al, *Quantitative study of tissue-engineered cartilage with human bone marrow mesenchymal stem cells, Arch Facial Plast Surg.,* 2005, 7:7-11.

One difference in the gene-expression profile of differentiated MPCs has been noted in the present study. PPARγ2, which is an indicator of adipogenic differentiation in bone marrow-derived mesenchymal stem cells, is also upregulated by osteogenic induction of traumatized muscle-derived mesenchymal progenitor cells. The effect of PPARγ2 on the MPCs does not appear to be anti-osteogenic as there is strong evidence from the histological and gene-expression findings that cells underwent osteogenic induction. In fact, the regulatory pathways governing PPARγ2 activity can modulate its anti-osteogenic function (Lecka-Czemik B, et al, *Divergent effects of selective peroxisome proliferator-activated receptor gamma 2 ligands on adipocyte versus osteoblast differentiation, Endocrinology,* 2002, 143:2376-84) and may represent a tissue-specific feature of regenerative cells that are present in muscle tissue.

Surgical debridement of open wounds is a medical and surgical necessity. Although removal of tissue from wounds that are characterized by substantial tissue loss is counterintuitive, it is essential for definitive treatment, wound closure, and proper healing. Granick M, et al, *Toward a common language: surgical wound bed preparation and debridement. Wound Repair Regen,* 2006, 14 Suppl 1:S1-10; Gregory P, et al, *The management of severe fractures of the lower extremities. Clin. Orthop Relat Res.* 1995; 318:95-105; Jacob E, et al, *A retrospective analysis of open fractures sustained by U.S. military personnel during Operation Just Cause. Mil Med.,* 1992, 157:552-6. The results of the present study suggest that this waste tissue may possess cellular building blocks that might be useful in future treatment and tissue-regeneration strategies. Although MPCs have been theorized to occupy traumatized muscle and their presence has been demonstrated in animal models, to our knowledge, the present report is the first to describe and characterize these cells in human tissues.

Qu-Petersen and colleagues described the presence of a population of progenitor cells obtained from skeletal muscle in a mouse model that exhibited characteristics similar to, but distinct from, mesenchymal stem cells. Qu-Petersen Z, et al, *Identification of a novel population of muscle stem cells in mice: potential for muscle regeneration. J. Cell Biol.* 2002, 157:851-64. They isolated a cell population by a preplating technique, which selects for the least-adherent cell population after a series of six serial platings. With this method, we were unable to obtain multiprogenitor cells from human tissue samples, and the cells that were obtained differed significantly from the multiprogenitor cells described here. Instead, we selected the most adherent cells two hours after initial plating and expanded the isolated cells in a culture medium identical to that used for bone marrow derived mesenchymal stem cells. The MDSCs identified by Qu-Peterson et al. were identified primarily on their ability to undergo myogenic differentiation and they express myogenic specific markers, e.g., MYOD, MCAM, desmin, etc. In contrast, MPCs do not undergo myogenic differentiation, nor do they express myogenic specific markers. MPCs and MSCs can be differentiated from each other based on their gene expression profiles. Jackson, W. M. et al., "*Putative Heterotopic Ossification Progenitor Cells Derived from Traumatized Muscle,*" J. Orthopaedic Res. (Jun. 10, 2009) (www.interscience.wiley.com; DOI 10.1002/jor.20924). For example, relative to MSCs, MPCs express significantly greater levels of TGFB3; MPCs continue to proliferate while being induced to differentiate into osteoblasts, and express lower levels of osteocalcin, an osteoblastic gene that is expressed during later stages of osteogenic differentiation. Additionally, there are differences in the osteogenic gene expression profile between the MPCs and MSCs, which may reflect the tissue of origin for both cell types. MPCs express higher levels of COL15A1, a gene associated with muscle tissue development, and GDF10, shown to be a negative regulator of osteogenesis, whereas the bone-marrow derived MSCs express higher levels of genes associated with bone physiology and maintenance: VEGFA 17, VCAM1 18 and IGF2 19. These differences may also reflect the fact that traumatized muscle-derived MPCs are harvested from an active wound bed, where they likely participate in the process of muscle tissue repair. During osteogenic differentiation, COL15A1 and GDF10 are substantially down-regulated, while VEGFA, VCAM1 and IGF2 are similarly up-regulated, suggesting that the MPCs can assume the role of osteoprogenitors under the appropriate biological environment, in a manner similar to other populations of MSCs.

The traumatized muscle-derived MPCs are of particular benefit in blast trauma-induced injuries given the high prevalence of heterotopic ossification associated with such injuries. E.g., Potter B K, et al., *Heterotopic ossification following traumatic and combat-related amputations. Prevalence, risk factors, and preliminary results of excision, J Bone Joint Surg Am.* 2007, 89:476-86. The osteogenic potential of these cells suggests their possible role in pathological processes that result in ectopic bone formation. Granick M, et al, *Toward a common language: surgical wound bed preparation and debridement, Wound Repair Regen.* 2006, 14 Suppl 1:S1-10.

Traumatized muscle tissue contains MPCs that can be harvested and expanded in vitro. This cell type may be used in reconstructive efforts or in cell-based tissue-engineered constructs for bone, tendon, cartilage, and fat. Multipotent adult stem cells are already being employed for orthopaedic reconstructive procedures; for example, bone-marrow aspirates have been used to augment bone defects, and intraoperative isolation systems have been used to augment fracture fixation and spine fusions with additional mesenchymal stem cells. Kumagai K, et al, *Circulating cells with osteogenic potential are physiologically mobilized into the fracture healing site in the parabiotic mice model, J Orthop Res.* 2008; 26:165-75; Muschler G F, et al. *Selective retention of bone marrow-derived cells to enhance spinal fusion. Clin Orthop Relat Res.* 2005; 432:242-51; Sen M K, et al., *Autologous iliac crest bone graft: should it still be the gold standard for treating nonunions? Injury,* 2007, 38 Suppl 1:S75-80.

In one embodiment, a method for isolating MPCs comprises: structural degradation or destruction (e.g., mincing or chopping) of a muscle sample from a wound (e.g., a debrided wound); suspension of the sample in a digestion medium; culturing and/or incubating the sample; and isolating MPCs.

In another embodiment, a method for isolating MPCs comprises: removal of unhealthy tissue (e.g., fat, fascia, damaged connective tissue, and necrotic tissue) from a healthy margin of muscle in a wound; isolation of a sample of the muscle; washing the muscle sample; structural degradation or destruction (e.g., mincing or chopping) of the muscle sample to create a tissue suspension; washing the tissue suspension of the sample in a digestion medium; and culturing and/or incubating the sample; and isolating MPCs. In one embodiment, the tissue is repeatedly washed in a salt solution (e.g., Hanks' Balanced Salt Solution (Gibco, Carlsbad, Calif.)).

In another embodiment, the tissue sample is chopped or minced in digestion medium (e.g., Dulbecco's Modified Eagle Medium (Gibco)), to which antibiotic may be added (e.g., penicillin/streptomycin/Fungizone (Gibco)). Mincing or chopping of the sample is carried out until an appropriate particle size is achieved, e.g., about 5 mm$^3$ or less, or about 1 mm$^3$, or such that the product can pass through a pipette). The minced tissue can then be transferred to digestion medium, e.g., containing Dulbecco's Modified Eagle Medium, 3× penicillin/streptomycin/Fungizone, and 0.5 mg/mL collagenase type 2 (Worthington Biochemical, Lakewood, N.J.)). The tissue slurry can then be cultured and/or incubated. In one embodiment, the tissue slurry is agitated at about 37° C. for two hours. The resulting digest may then be filtered (e.g., through a 40-μm cell strainer (Falcon)). The resulting digest may also be subjected to centrifugation. A pellet resulting from a centrifugation step may be resuspended (e.g., in growth medium such as Dulbecco's Modified Eagle Medium with 10% fetal bovine serum; Gibco) and 5× penicillin/streptomycin/Fungizone).

The resulting digest and/or the resuspended pellet may be plated onto tissue culture and incubated. In one embodiment, incubation is carried out at elevated temperature (e.g., >25° C.; or >30° C.; or about 37° C.); and may be carried out in a $CO_2$-humidified environment (e.g., 1-10% $CO_2$; or about 5% $CO_2$). The incubation may be performed in a cell incubator (e.g., for at least about one-half hour; or for about two hours). Following incubation, the culture may be washed with a biologically compatible medium (e.g., with Hanks' Balanced Salt Solution). As a next step, a fresh growth medium may be added with additional antibiotic (e.g., 3× penicillin, streptomycin, & Fungizone). In one embodiment, when the multiprogenitor cell colony forming units are observed, the concentration of penicillin, streptomycin, & Fungizone is lowered to about 1×. In another embodiment, the cell cultures may be routinely passaged at 80% to 90% confluence and split (e.g., 1:4).

Figure 3:
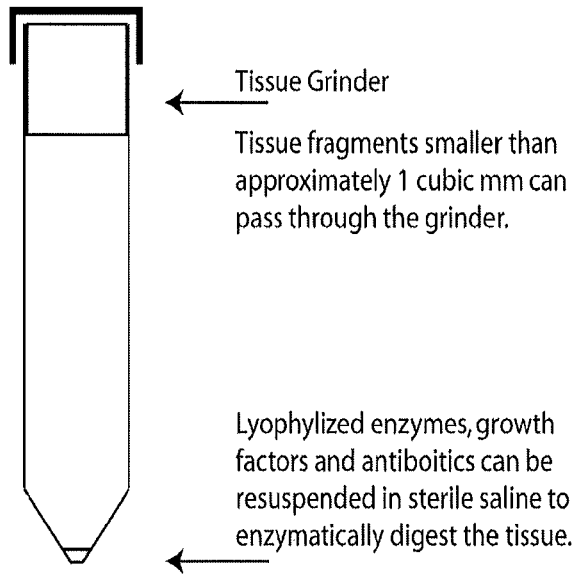
FIG. 3: Illustrates devices useful in MPC isolation in the form of tubes having a tissue grinder for structural degradation of muscle tissue from wound (Tube 1); and a tube having shear channels and a cell strainer (Tube 2).
Figure 3:
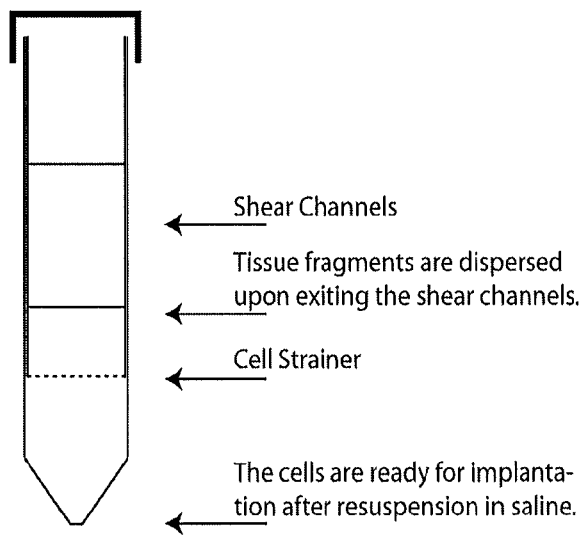

In another embodiment, the present invention provides methods and devices to harvest MPCs from wound tissue. One such method deploys two chambers or tubes. The chambers may be configured in shape and size as a conventional centrifuge tube. See FIG. 3. As such, a first tube is outfitted with a tissue grinding device, optionally near an opening of a tube. The grinder chops or minces MPC-containing tissue (e.g., to about 5 mm$^3$ or less, or about 1 mm$^3$ or less). Interior to the grinder within the chamber is a reservoir of a medium containing enzymes, growth factors, antibiotics, and other suitable cell-sustaining agents. Optionally, those agents are suspended in a sterile saline solution, and the tissue fragments are enzymatically digested. The digestion may occur over an incubation period, optionally at elevated temperature (e.g., >25° C.; or ~37° C.). Following incubation, the digested tissue is processed through another chamber, device or tube. Here, the second chamber is outfitted with a series of shear channels, which cause the digested tissue fragments to disperse. The resulting tissue fragments then are processed through a cell strainer, which isolates the MPCs. The isolated MPCs are then suitable for implantation and use in the various methods and devices disclosed elsewhere herein, and in other methods and therapies as would occur to one of ordinary skill in the art. Such methods and therapies can be readily adapted to be performed at the point-of-care.

Progenitor cells (MPCs) harvested from traumatized muscle have several characteristics of MSC: 1) similar morphology, proliferation rate, cell surface markers and gene expression profile; 2) differentiation into osteoblasts, adipocytes and chondrocytes; and 3) immunosuppressive, pro-angiogenic, anti-fibrotic properties. Additionally, the differentiation potential of MPC populations is uniform between patients; and traumatized muscle-derived MPCs could be harvested clinically for use in regenerative medicine applications, e.g., cellular therapy and tissue engineering.

We also provide various grafts that can be used to promote healing of an injury or defect in nerve, bone, or vascular tissue. We have discovered that MPCs produce various bioactive agents that promote healing and regeneration, such as growth factors or differentiation factors, and/or promote the migration of other healing influences to the site of the injury or defect such as other cell types (e.g., Schwann cells), or that promote the actual differentiation of other cell types into lines needed to regenerate or restore injured or damaged tissue. The grafts are configured to place MPCs in proximity to the injury or defect, and in fluid contact with the injury or defect such that the agents produced and/or secreted by MPCs produce the intended effect at or within the injury. The grafts differ from other grafts incorporating other multiprogenitor cells such as stem cells in that the instant grafts avoid or diminish access or contact of the MPCs, per se, to the site of the injury or defect. That is, the wound, injury, or defect is not treated by applying the MPCs within the injury or defect with the idea that those cells will differentiate into the cell types needed to fill the gap or eliminate the defect. Rather, they are placed proximate, but outside, the actual defect, and in fluid communication with the defect, such that the biologically active agents and factors can migrate to the defect and promote the body's natural healing and/or regeneration processes. By promoting those processes, injuries or defects are healed more promptly, and injuries that might not otherwise be able to heal at all are effectively treated.

The scaffold component of these grafts generally has a structure including a matrix material that is porous in which the MPCs are seeded. The matrix material is made of non-aligned fibers that form many discrete interstices or voids, which, due to the complex topology of the matrix serve to retain the MPCs. The MPCs can be implanted within the matrix by passive infusion, by mechanical injection or introduction into the interior of the matrix, or by cultivating the cells to grow within the matrix, or some combination thereof. Additionally, the cells can be fixed more stringently within the matrix by chemical modification of the matrix to increase the coefficient of friction between the matrix and the cells, or by increasing the chemical attraction or bonding (e.g., covalent or ionic) between the matrix and the MPCs.

The structure of the matrix is highly adaptable, and can be modified to whatever shape and dimension is best suited to put the MPCs proximate and in fluid contact with the injury or defect. Thus, the MPC-seeded matrix can be in the form of a patch, wrap, conduit, or the like. Additionally, patches and wraps can be further modified and configured to fit the contours and dimension of the wound as in any bandage or wound treatment. The matrix can be further modified in accordance with known principles to be used internally or externally.

The shape and dimension of the matrix can be further modified to complement other structural features of the graft. For example, and as discussed elsewhere herein, the matrix can be made to serve as an outer sheath of a conduit, wrapping around, enveloping, or overlaying structural features that might serve as scaffolding for tissue growth.

Also provided is a graft comprising a porous matrix of non-aligned fibers forming interstices; the interstices consisting of a cellular component and a non-cellular component, and wherein the majority of the cellular component is MPCs; a conduit internal to the matrix; and wherein the interior of the conduit is in fluid communication with the matrix. In one embodiment, there will be a level of fluid communication between matrix and the interior of the conduit. It is contemplated that the permeability will permit migration of various factors secreted by MPCs into the conduit, but generally retain a flow of fluid within and through the conduit.

The matrix, aligned fibers, conduit, or other elements of the grafts disclosed herein can be formed of any known and adaptable biocompatible structural material that lends itself to fabrication according to the demands of the end use. In some embodiments, the material is a synthetic structural material such as a biocompatible polymer. Biodegradable polymers are also desirable. Those materials can be selected such that they are dissolved or resorbed by the body without the need for surgical removal procedures. Biocompatible, biodegradable materials useful in the grafts disclosed herein include polyglycolic acid (PGA), type 1 collagen, Poly-DL-lactide-caprolactone (PCL), laminin, gelatin, and the like.

The graft may further comprise a liquid impermeable exterior liner overlaying the matrix. In one embodiment, the impermeable exterior liner isolates the fluid and cells of the interior of the conduit with the external media. Impermeable generally refers to fluid impermeable, though it also contemplates a less than perfectly fluid impermeable membrane.

Among other things, the exterior liner can be used to seal the interior of the graft. This will be advantageous in vascular grafts. The exterior liner can also be configured to include additional structural elements such as flanges, sleeves, connectors, and other sealing means. Those additional structural elements can be configured to create a connection or, alternatively, a seal between the biological conduits of the vasculature and the conduit of the graft, and to isolate the contents of the two from external biological media. Connecting elements used to effect a seal or connection between the graft and vasculature (or other conduit) can be fabricated from the same material as the impermeable exterior liner, or may be fabricated of another material, and may be part of yet another layer or structural element altogether.

We have also devised a novel nerve graft device or a nerve tube. The nerve tube comprises several chambers or sheaths (e.g., two or more). The tube may comprise two sheaths, which may in turn be surrounded or encased within a conduit wall, which may optionally provide a fluid-impermeable exterior wall thus isolating the nerve tube and its contents from the exterior environment. The inner sheath comprises aligned fibers generally parallel to a longitudinal axis of symmetry through the tube. The fibers may be nanofibers. The sheath of aligned fibers is surrounded by another sheath containing random or non-aligned and/or non-linear fibers. The inner and outer sheaths may be in fluid communication. The exterior wall may extend in length beyond the inner and/or outer sheaths. In such an embodiment, the tube may be placed around a proximal and/or distal nerve stump, optionally enclosing and isolating a space between the stumps.

In one embodiment, the nanofibers are oriented within an inner sheath at the core of a generally tubular structure having an inner sheath and an outer sheath. The tubular structure may be circular or elliptical, or any shape necessary to align the nerve tube with the injured or damaged nerves needing repair or regeneration.

The inner sheath constitutes aligned fibers paralleling an axis of symmetry through the center of a tube. The aligned fibers may be linear, parallel fibers less than about 100 µm, or less than about 10 µm, and running the length of the tube. The nanofibers create sub-micron sized scaffolding that provides a structural framework supporting the growth of nerve regeneration elements, e.g., axons, along the length of the nerve tube or graft. As such, the aligned fibers provide three dimensional support and directional orientation for the growing axon. The aligned fibers may be made of a biocompatible, biodegradable material that is resorbed or dissolved within the body avoiding the need for surgical removal.

The nerve tube or graft device further includes a three-dimensional matrix in an outer sheath of the graft. The outer sheath of the nerve tube or graft device surrounds the aligned nanofibers, and may permit fluid exchange between the two. The outer sheath may share an axis of symmetry with the nerve tube, and may be generally concentric with the bundle of aligned fibers of the inner sheath. By "aligned fibers" is meant that the fibers are generally aligned along a longitudinal axis of the inner sheath or tube. The fibers are not necessarily strictly parallel, and some deviation in direction and linearity is contemplated.

The material of the outer sheath provides a support matrix for multipotent cells, particularly MPCs, within the outer sheath. The multipotent cells can be MPCs alone or in combination with MSCs and/or other regenerative cells.

In one embodiment, the nerve tube comprises a tube comprising two zones or sheaths. The zones or sheaths may be coaxial. The inner sheath may comprise aligned fibers generally parallel to an axis of symmetry along the length of the nerve tube. The ends of the aligned fibers are exposed to the exterior of the tube permitting axonal growth along the fibers through the tube.

Surrounding the inner sheath, and optionally in fluid contact therewith, is an outer sheath comprising non-aligned and/or non-linear fibers. The fibers of the two sheaths may be of the same or different material, and may or may not be of the same size, shape, diameter, and dimension. Either or both of the sheaths of the nerve tube may further comprise biologically active agents in addition to those secreted by MSCs and/or MPCs, e.g., hormones, steroids, anti-inflammatories, analgesics, immunosuppressives, anticoagulants, muscle relaxants and antispasmodics, antibiotics and/or antimicrobials, growth factors, colony stimulating factors, nutrients such as vitamins, peptides, small drug molecules, gene therapy agents, e.g., plasmids, retrovirals, and combinations thereof; and other pharmacologically acceptable excipients, diluents, buffers, preservatives, and the like. Either or both of the sheaths may further comprise growth media and/or nutrients, antibiotics, preservatives, buffers, and the like to maintain viability of the MSCs and/or MPCs. Other multipotent cells may also be included.

Also provided is a method of forming a nerve graft in a patient suffering an injury to a nerve comprising: seeding a nerve guide or tube with MPCs; and implanting the nerve guide between a proximal nerve stump and a distal nerve stump. The implant may be removed following regeneration of the nerve; or the implant may be made of a resorbable material eliminating the need of a surgical removal process. The nerve guide is constructed and/or implanted such that it resides proximate to the nerve stumps, and bridging the gap between the nerve stumps. Thus, each end of the nerve guide or tube connects the nerve.

The nerve guide or tube is maintained in position relative to the nerve stumps for a period sufficient to guide axonal growth and restoration between the respective nerve stumps. As used herein, the term "nerve stump" refers to the one or more residual portions of a nerve following injury or damage to the nerve resulting in a loss of function, e.g., as by severed axon. Nerve injury may be in the form of traumatic injury, surgery, the result of disease, or other cause. In one embodiment, the nerve guide is a peripheral nerve guide as disclosed elsewhere herein.

We have also developed a peripheral nerve guide. The guide can be used to bridge a critical sized defect in a peripheral nerve following traumatic injury.

In one embodiment, the device has at least two components (see, e.g., FIG. 1). First, is a cellular scaffold. The scaffold can be fabricated using polycapralactone, or other suitable biocompatible and/or biodegradable polymer such as polylactic acid, collagen, laminin, gelatin, and the like. The polymer is formed into nano-meter scale fibers (e.g., about 50-500 nm diameter; or about 100-300 nm diameter; or about 200 nm diameter). In one embodiment, the scaffold is formed by extrusion of polymer using an electrospinning process. However, it will be appreciated by those skilled in the art that other methods of fabricating such fibers are available, and thus are contemplated herein.

The scaffold contains a core of aligned nanofibers, which guide and support growing axons to bridge the defect in the nerve. The aligned fibers may be surrounded by a sheath of non-aligned, randomly oriented fibers. MPCs may be seeded in the sheath of non-aligned fibers. Among other things, MPCs can be cultured to secrete biochemical factors. Those factors enhance the growth rate of axons, and recruit native neuronal support cells into the device. MPCs can be used as the only active growth promoting agent within the scaffold, or in combination with other agents, including other multipotent cells such as stem cells, including MSCs. Alternatively, other agents and/or multipotent cells can be used in the place of MPCs, and those too can be employed alone or in combination with other biologically active agents, including those fostering and/or promoting the growth of bone and/or other tissue. Thus, the instant scaffold or grafting device is not limited to nerve grafts, but may be used to repair various injuries including bone, blood vessel, muscle, ligament, and tendon.

Among other things, the grafts disclosed herein assist nerve regeneration. They provide a protective environment for axonal sprouting and improve the chances that the damaged axons will reach the distal nerve stump. Biocompatible, biodegradable materials useful in the grafts disclosed herein include polyglycolic acid (PGA), type 1 collagen, Poly-DL-lactide-caprolactone (PCL).

The instant grafts have the particular advantage of providing individual axon guidance with nanofiber filaments, and facilitate access and activity of axonal support cells such as Schwann cells or MSCs. Both of these features constitute improvements over currently available devices, and enhance the speed of axonal growth. The speed and accuracy of axonal growth determines the success of reinnervation. The instant devices provide improved regeneration of peripheral nerves compared to the currently available alternatives. Furthermore, by increasing the speed of axonal growth, the instant nerve guides and methods expand the versatility and range of nerve regeneration; and enable regeneration of nerves suffering defects of substantially greater size than has been possible under prior therapies.

In one embodiment, the first device comprises a solid core of aligned nanofibers. The nanofibers support growth of regenerating axons. Although the use of aligned fibers has been shown to accelerate the rate of axonal growth, such use of fibers has been limited. A technique used to fabricate a sheet of aligned fibers has been reported, and previous investigators have cut strips of these aligned fibers and pulled them through the lumen of a conventional nerve guide. Those strips or sheets of aligned fibers afford only a two dimensional framework, and diminishes migration of Schwann cells into the lumen. That has the effect of diminishing growth of the axon through the lumen, and less effective regeneration of the nerve. While the axons that reach one of the strips of aligned nanofibers appear to grow faster and reach the distal nerve stump, this improved regeneration only accounts for a fraction of the total number of axons in the nerve. Those devices also suffer because the fibrin bridges that form naturally in an empty conduit are inhibited by the aligned sheets of fibers. Without the fibrin bridges, the Schwann cells are limited in their migration into the void therefore there is limited chemotaxis for axons to bridge the gap. Our device is designed to obviate the need for fibrin bridging as the scaffold for axon growth is already in place, and the MPCs seeded within the graft provide or enhance chemotaxis.

In at least one embodiment of the present invention, all of the regenerating axons have access to aligned nanofibers. This can be effected by surgically implanting the device so that it is contact with the two nerve stumps.

Figure 2:
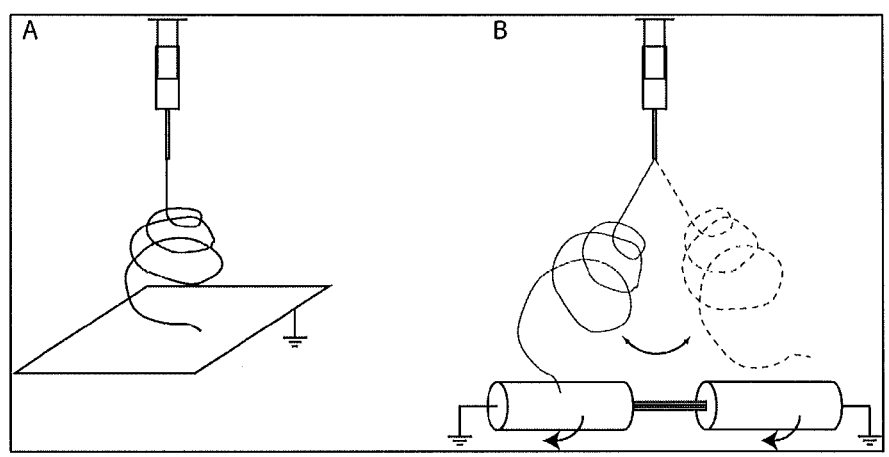
FIG. 2: One method of fabricating the device. (A) In an electrospinning setup, polymer fibers are extruded onto a grounding plate. (B) Two grounded axels are aligned end-on with the aligned nanofibers between them. The entire assembly is rotated as a mandrel, and the extruded nanofibers are attracted to the axels. As the extruded fibers stochastically switch their target between the two targets, the aligned nanofibers become encased in a non-aligned sheath.

In one embodiment, the device is formed by electrospinning the non-aligned sheath of nanofibers that surround the aligned core (FIG. 2). In one embodiment, electrospinning is performed by passing a polymer solution through a blunt-tipped needle that contains a high electric charge (e.g., greater than about 15 kV). As the solution passes through the needle, part of the charge is transferred to the polymers, which are extruded out of the needle towards a grounding plate. In one embodiment of the present invention, the grounding plate is replaced with two axels that are aligned end-on. In between the axels, there is a strip of aligned nanofibers, and the entire assembly is rotated as a mandrel. As the polymers are extruded from the charged needle, the resulting nanofibers are attracted to ground on one of the two axels, and the target axel can switch stochastically. As the extruded polymer fiber alternates between the two targets, the fiber is stretched over the strip of aligned nanofibers. Eventually, the aligned nanofibers become completely encased by the sheath of non-aligned fibers. This novel electrospinning process facilitates the formation of a device having an aligned core of fibers surrounded by non-aligned fibers to support the neural support cells.

In another embodiment, there is provided a method of treating a patient suffering an injury to tissue and requiring restoration and/or regeneration of the tissue comprising applying to the injury a graft comprising a porous matrix of non-aligned fibers forming interstices, the interstices consisting of a cellular component and a non-cellular component, and wherein the majority of the cellular component is mesenchymal progenitor cells. As used herein, the term interstices refers to voids among the fibers. The voids can be seeded with, or infused with, MPCs and other cell types, cell culturing components, and non-cellular components such as other active ingredients. Use of the term majority means greater than 50%.

In such methods, MPCs can be seeded within the graft such that the majority of MPCs are not in direct contact with the tissue requiring repair or regeneration. The treatment method contemplates that the MPCs are placed in proximity to the injury or damage site, but are not positioned or administered in such a way that they are used to pack a gap or defect in the tissue. That is, the MPC seeded matrix will not form a structural element restoring or regenerating the damaged or missing structural or function elements of the wounded tissue, but will be part of a separate matrix that is not ultimately incorporated into the gap or defect. Generally, the MPC-seeded matrixes described herein will be a biocompatible, biodegradable material that is dissolved or resorbed by the body, but preferably not until the gap or defect in the tissue is healed or sufficiently diminished that the body's natural healing capacity can take over and complete the healing and/or regeneration process.

Among other things, the methods and materials disclosed herein can be used to: prevent fibrosis; augment muscle regeneration; improve fracture healing. Devices can also be seeded with MPCs for tissue engineering, e.g., peripheral nerve; bone; blood vessel; tendons and ligaments.

EXAMPLES

Example 1

Muscle-Derived Mesenchymal Progenitor Cell Isolation

Mesenchymal Progenitor cells (MPCs) were harvested from traumatized human muscle debridements using a previously established procedure. Nesti L J, et al. *Differentiation potential of multipotent progenitor cells derived from war-traumatized muscle, J. Bone Joint Surg. Am.*, 90, 2390-98 (2008). MSCs were obtained from human bone marrow.

With institutional review board approval from Walter Reed Army Medical Center and informed patient consent, tissue specimens were obtained from patients who had sustained traumatic extremity injury during Operation Iraqi Freedom and Operation Enduring Freedom. These patients presented to Walter Reed Army Medical Center approximately three to seven days after the injury and underwent serial debridement and irrigation procedures until the wounds were determined to be clinically acceptable for definitive orthopaedic treatment. The amount and nature of debrided tissue was surgeon dependent and was based on trauma surgery principles of circumferential removal of all grossly contaminated, apparently necrotic, and nonviable tissue along with a thin margin of healthy-appearing tissue. This procedure was repeated at each surgical encounter until only healthy tissue remained, and cells typically were harvested from muscle tissue obtained during the second or third serial debridement.

The protocol for extracting muscle-derived multiprogenitor cells was based on a modification of previous work in isolating mesenchymal stem cells that was performed in our laboratory. Caterson E J, *Human marrow-derived mesenchymal progenitor cells: isolation, culture expansion, and analysis of differentiation. Mol. Biotechnol.* 2002; 20:245-56. Fat, fascia, other connective tissue, and necrotic tissue were dissected away from the healthy margin of the debrided muscle sample. Approximately 0.5 cc of the remaining muscle tissue was processed for cell extraction. The tissue was washed three times in Hanks' Balanced Salt Solution (Gibco, Carlsbad, Calif.) and then was extensively minced in a 10-cm culture dish containing Dulbecco's Modified Eagle Medium (Gibco) and 3× penicillin/streptomycin/Fungizone (Gibco) until it could pass through the tip of a 25-mL serological pipette (Falcon; BD Biosciences, San Jose, Calif.). The minced tissue was transferred to a 50-mL conical vial with digestion medium containing Dulbecco's Modified Eagle Medium, 3× penicillin/streptomycin/Fungizone, and 0.5 mg/mL collagenase type 2 (Worthington Biochemical, Lakewood, N.J.). The tissue slurry was agitated gently at 37° C. for two hours, and the resulting digest was filtered through a 40-μm cell strainer (Falcon), pelleted by means of centrifugation, resuspended in growth medium (Dulbecco's Modified Eagle Medium with 10% fetal bovine serum; Gibco) and 5× penicillin/streptomycin/Fungizone, and then plated onto tissue culture polystyrene (150-cm² flask; Falcon). The cells were incubated at 37° C. in a 5% $CO_2$-humidified cell incubator for two hours and then were extensively washed with Hanks' Balanced Salt Solution before fresh growth medium was added with 3× penicillin/streptomycin/Fungizone. Once multiprogenitor cell colony forming units were observed, the concentration of penicillin/streptomycin/Fungizone was lowered to 1×. Cell confluence was obtained after approximately two weeks. The cell cultures were routinely passaged at 80% to 90% confluence and split 1:4.

Adult human bone marrow-derived mesenchymal stem cells were isolated as described previously (Caterson E J, *Human marrow-derived mesenchymal progenitor cells: isolation, culture expansion, and analysis of differentiation. Mol. Biotechnol.* 2002; 20:245-56) with use of bone marrow obtained from the medullary canal of long bones from patients undergoing elective total hip replacement. The cells were then washed and plated onto tissue culture polystyrene.

Example 2

Differences Between MPCs and MSCs

A. Gene Expression Profile Differences (Osteogenic)

Figure 4:
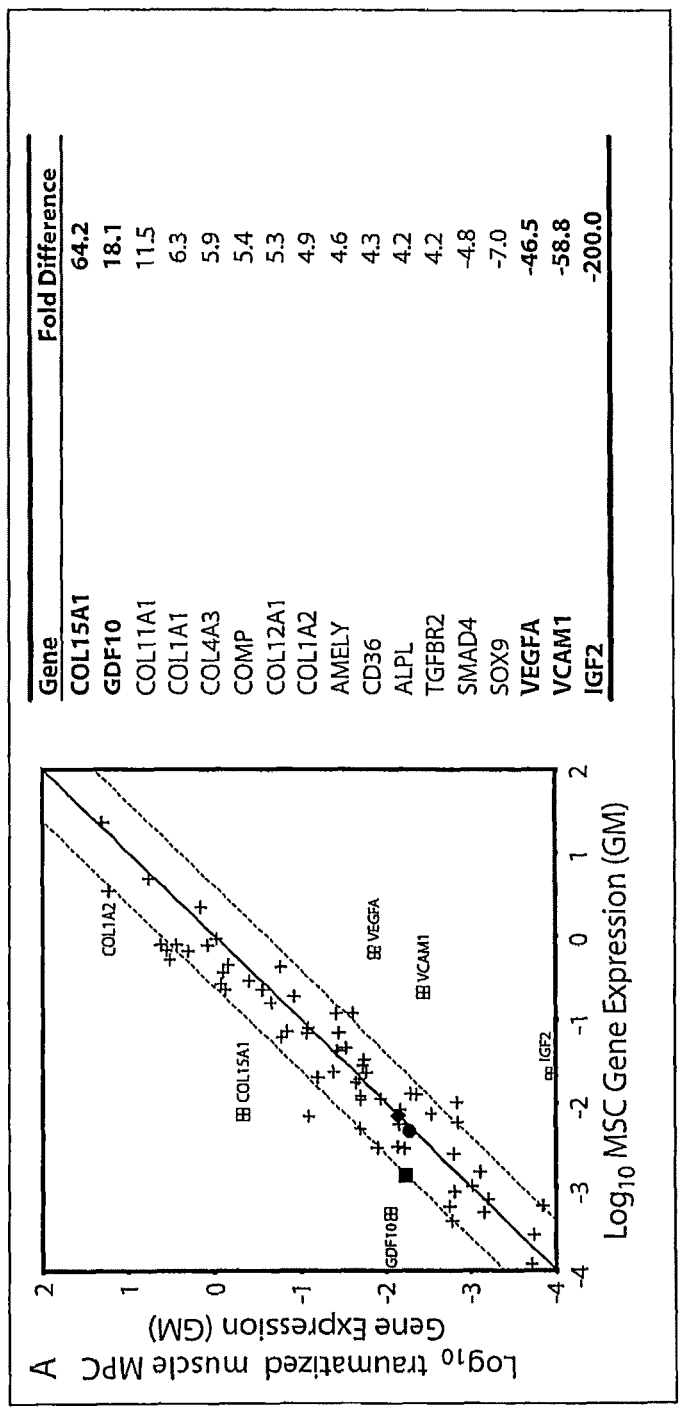
FIG. 4: Osteogenic gene expression profile. A: The differential gene expression of 84 genes related to osteogenesis in MPCs compared to MSCs cultured in growth medium. The table lists all genes that are differentially expressed more than five-fold. Circles (●) represents RUNX2, squares (■) represent ALP and diamonds (♦) represent BGLAP (Osteocalcin) expression. Genes differentially expressed significance $p<0.018$ (Student's t-test with $n=3$) are drawn inside a box in the plot and are written in bold in the table.

Significant differences were noted between the traumatized muscle-derived MPCs and bone marrow-derived MSCs (FIG. 4). First, the MPCs continue to proliferate while being induced to differentiate into osteoblasts. There is evidence supporting that the entire population of MPCs is slow to shift from the proliferative state to differentiation, since histological evidence of differentiation appears homogeneous throughout the MPC cultures undergoing osteogenesis. These cells also express lower levels of osteocalcin, an osteoblastic gene that is expressed during later stages of osteogenic differentiation. Second, there are differences in the osteogenic gene expression profile between the MPCs and MSCs cultured under growth conditions, which may reflect the tissue of origin for both cell types. MPCs express higher levels of COL15A1, a gene associated with muscle tissue development, and GDF10, shown to be a negative regulator of osteogenesis, whereas the bone-marrow derived MSCs express higher levels of genes associated with bone physiology and maintenance: VEGFA, VCAM1 and IGF2. These differences may also reflect the fact that traumatized muscle-derived MPCs are harvested from an active wound bed, where they likely participate in the process of muscle tissue repair. During osteogenic differentiation, COL15A1 and GDF10 are substantially, albeit non-significantly, down-regulated, while VEGFA, VCAM1 and IGF2 are similarly up-regulated, suggesting that the MPCs can assume the role of osteoprogenitors under the appropriate biological environment, in a manner similar to other populations of MSCs.

B. Gene Expression Profile Differences (MSC Biology)

Figure 5:
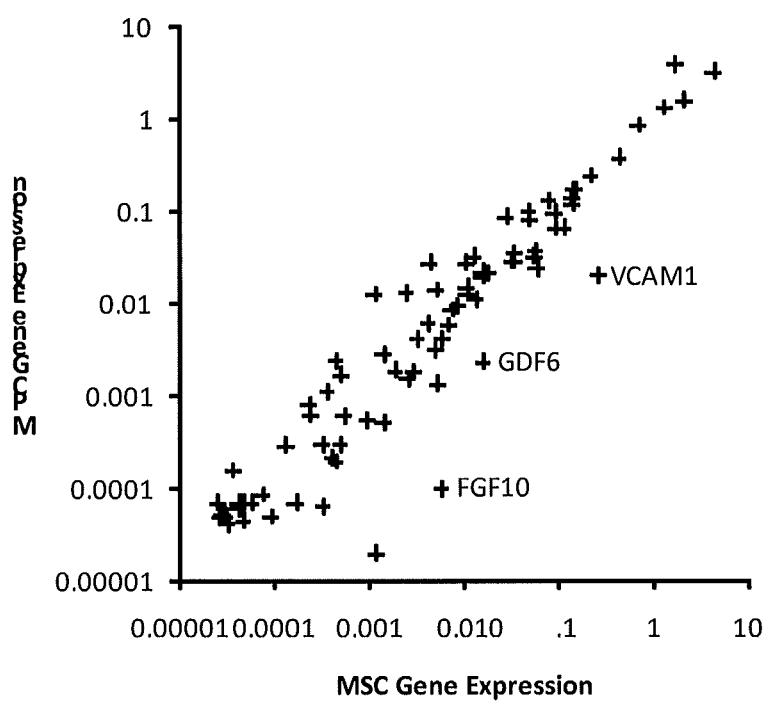
FIG. 5: MSC gene expression profile. The differential gene expression of 84 genes related to MSC Biology in MPCs compared to MSCs. Genes differentially expressed significance $p<0.05$ (Student's t-test with $n=3$) are labeled.

Three specific genes associated with MSC were differentially regulated between MPCs and MSCs (FIG. 5). FGF10 is a gene associated with development and the initiation of wound healing, GDF6 codes for a cytokine that works in concert with bone Morphogenic proteins, and VCAM1 provides a molecular adhesion to vascular structures. The VCAM1 result corroborates the finding from the previous experiment. These genes may play a role in the ability of MSCs to reside in the bone marrow and detect damage to the bone.

C. Differences in Cell Surface Epitope Profiles of MSCs and MPCs Immunophenotyping Mouse anti-CD29 monoclonal IgG (clone Ha2/5), mouse anti-CD44 monoclonal IgG (clone IM7), mouse anti-CD105 monoclonal IgG (clone 35), and mouse anti-CD146 monoclonal IgG (clone P1H12) antibodies and phytoerythrin-conjugated mouse anti-CD45 monoclonal IgG (clone TU116), mouse anti-CD73 monoclonal IgG (clone AD2), mouse anti-CD90 monoclonal IgG (clone 5E10), and mouse anti-CD105 monoclonal IgG (clone 35) antibodies were obtained from BD Biosciences (San Jose, Calif.). All antibodies were reactive against human antigens. Donkey anti-mouse IgG conjugated with fluorescein isothiocyanate were obtained from Jackson ImmunoResearch (West Grove, Pa.). Testing with negative and positive controls confirmed the specificity of these antibodies.

Cells used for staining were cultured in growth medium on glass coverslips for fourteen days during the second or third passage. They were washed once with Hanks' Balanced Salt Solution and then were fixed in 3% phosphate-buffered paraformaldehyde for twenty minutes. Fixed cells were first blocked in 2% bovine serum albumin (Sigma-Aldrich, St. Louis, Mo.) for thirty minutes and then were incubated with the respective primary antibodies in phosphate-buffered saline solution (diluted 1:100) with 1% whole donkey IgG for two hours at room temperature or overnight at 4° C. and then with fluorescein isothiocyanate-conjugated secondary antibodies (diluted 1:100) and DAPI (4',6-diamidino-2-phenylindole; Invitrogen, Carlsbad, Calif.; diluted 1:10,000) in phosphate-buffered saline solution for thirty minutes. The coverslips were then mounted to slides with VECTASHIELD (Vector Laboratories, Burlingame, Calif.) and viewed with a Zeiss 510 Metaconfocal laser scanning microscope (Carl Zeiss Microimaging, Thornwood, N.Y.).

During the second passage, approximately 250,000 cells were plated in a 150-cm2 cell-culture flask for flow cytometric analysis. When the cultures were approximately 80% confluent, the cells were rinsed once with Hanks' Balanced Salt Solution and then were lifted off the surface with 0.25% trypsin and were transferred to a 50-mL centrifuge tube. The tube was centrifuged for five minutes at 200 g, the supernatant was aspirated, and the pellet was resuspended in (fluorescence activated cell-sorting) buffer (0.1% bovine serum albumin and 0.01% sodium azide in Hanks' Balanced Salt Solution). Next, 100 µL of the cell suspension was aliquoted into fluorescence activated cell-sorting tubes, and the phytoerythrin-conjugated antibodies (CD14, CD73, CD90, CD105, and an isotype control; BD Biosciences) were added to each tube at a 1:50 dilution.

The cells were incubated in the dark at 4° C. for forty minutes, washed once in fluorescence-activated cell-sorting buffer, and resuspended in 100 µL of fresh fluorescence-activated cell sorting buffer. The fluorescent intensity profiles of the cells were analyzed by means of fluorescence-activated cell-sorting with use of a FACSCalibur flow cytometer (BD Biosciences).

Figure 6:
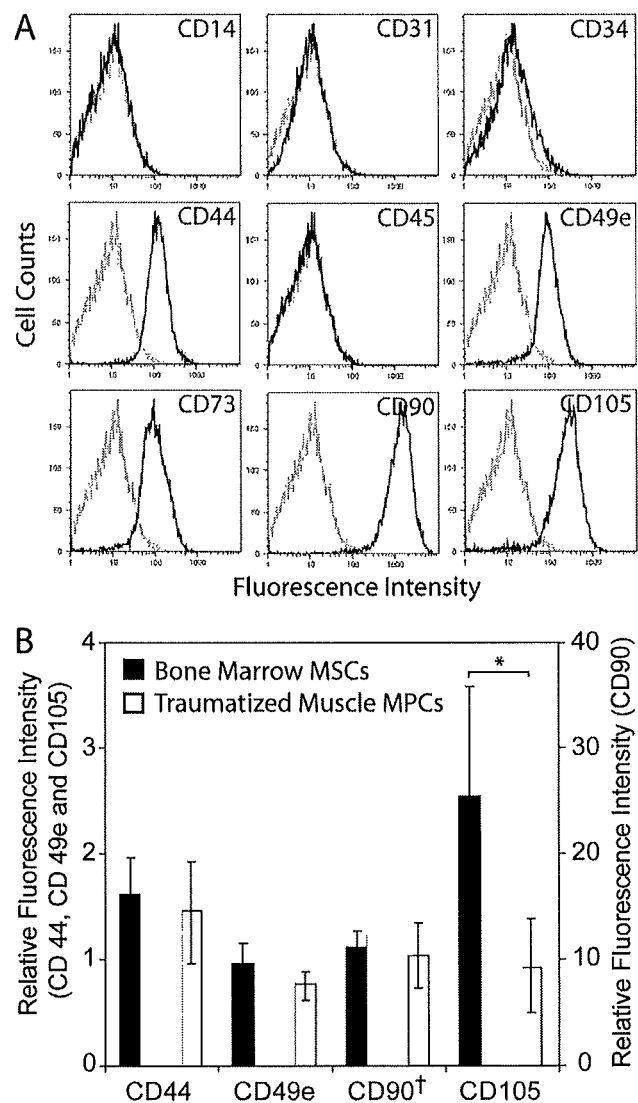
FIG. 6: Immunophenotyping of MPCs. A: The MPCs were positive for CD44, CD49e, CD73, CD90 and CD105 and negative for CD14, CD31, CD34 and CD45. The fluorescence intensity of each marker (black lines) compared to the isotype control (grey lines). B: The fluorescence intensity of each cell-surface marker was normalized against the fluorescence intensity of CD73. The CD105/CD73 ratio was significantly greater for MPCs than bone-marrow derived MSCs ($p=0.01$). †The CD90/CD73 ratios are shown scaled by a factor of 10 and the values correspond to the right axis.

The MPCs were positive for CD44, CD49e, CD73, CD90 and CD105 and negative for CD14, CD31, CD34 and CD45. The CD105/CD73 ratio was significantly greater for MPCs than bone-marrow derived MSCs (p=0.01) (FIG. 6). This experiment demonstrates that even though the MPCs are positive for cell surface markers that are also present on MSCs, they are expressed at different levels on the cell surface.

Example 3

MPC In Vitro Expression of Trophic Factors

A. Neurotrophic Factor Gene Expression

In 2-D culture, the progenitor cells derived from traumatized muscle were exposed to defined glial-induction media. Conditions to optimize the neurotrophic potential of MSCs and muscle-derived progenitor cells were determined using ELISAs to measure the concentration of secreted neurotrophic factors (i.e., BDNF: Brain Derived Neurotrophic Factor, NGF: Nerve Growth Factor, GDNF: Glial Derived Neurotrophic Factor, etc,).

The cells were capable of producing substantial amounts of neurotrophic factors, even without neuroglial induction. After 7 days in defined conditions for glial differentiation, the progenitor cells began to produce neurotrophic factors. In particular, the progenitor cells could produce substantial amounts of BDNF when cultured under optimal induction conditions. Evidence also suggests that they expressed Glial Fibullary Acid Protein, a glial cell specific marker. The amount of CNTF produced by the progenitor cells was unaffected by the neuroglial induction media. MPCs may also express nestin following neurotrophic induction, and the percent of nestin positive cells appears to increase following neurotrophic induction. Pre-treatment with retinoic acid (RA) and β-mercaptoethanol (BME) significantly increases the production of BDNF in progenitor cells cultured in GM, but not as much as the cells in the optimal neuroglial/neurotrophic induction medium. Pre-treatment with RA and BME had no effect on the cells in neuroglial differentiation media.

Figure 7A:
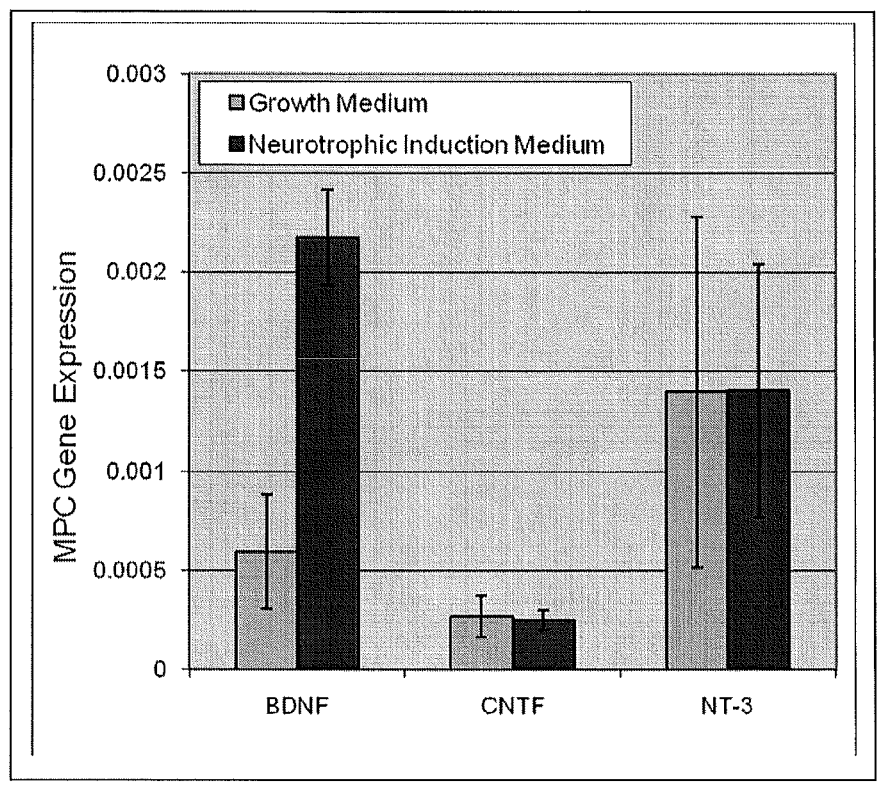
FIG. 7: MPC Neurotrophic Factor Expression. A. RT-PCR analysis of neurotrophic factor gene expression in traumatized muscle MPCs. B. Protein level measurement of neurotrophic factor production in traumatized muscle MPCs.
Figure 7B:
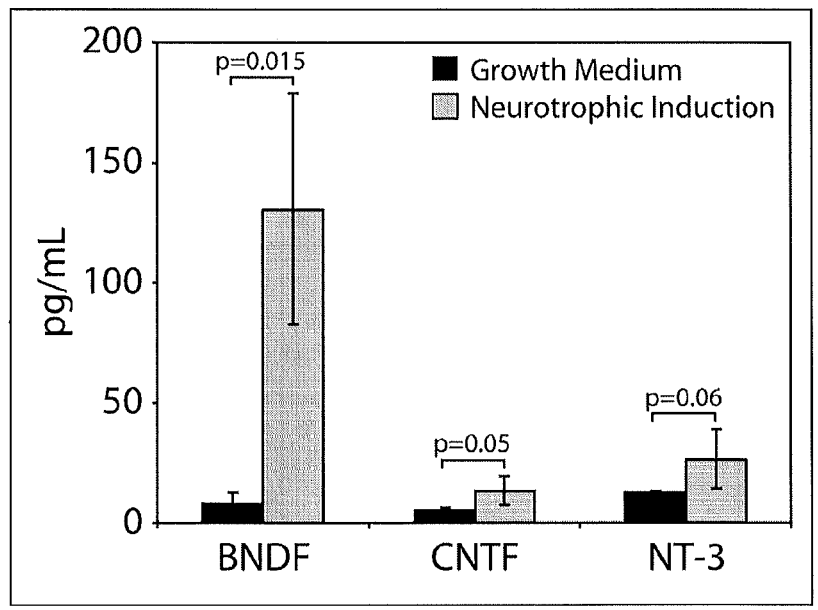

The final system of neurotrophic induction includes pre-treatment with RA, followed by 7 days in the optimized neurotrophic induction media. This system increased the production of BDNF and two other neurotrophic factors important to peripheral nerve regeneration: CNTF and NT-3 (FIG. 7).

TABLE 1

Formulations for the Neuroglial-Induction Media

| Media | Formulation |
|---|---|
| GM | DMEM with 10% FBS |
| NM0 | Neurobasal Medium with 2% B27 Supplement |
| NM1 | Neurobasal Medium with 2% B27 Supplement, 5 µM cAMP, 5 µM IBMX, 2.5 µg/mL Insulin and 25 ng/mL NGF |
| NM2 | Neurobasal Medium with 2% B27 Supplement, 10 ng/mL bFGF, 20 ng/mL EGF and 10 ng/mL of LIF |
| NM3 | αMEM with 10% FBS, 5% Horse Serum, 50 µM Hydrocortisone and 0.1 µm Dexamethasone |
| NM4 | DMEM/HAMS F12 with 2% B27 Supplement, 2% FBS, 20 µM Retinoic Acid and 10 ng/mL bFGF |

B. MPC vs. MSC Expression of Other Specific Trophic Factors and Cytokines

Figure 8:
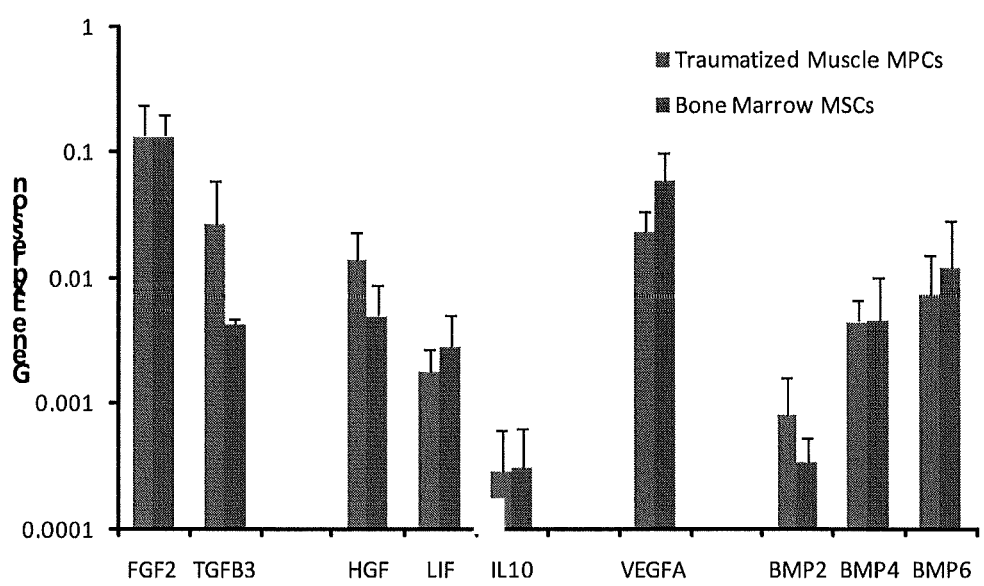
FIG. 8: Gene expression of trophic factors secreted by MPCs and MSCs.

Despite the specific differences in gene expression and cell surface epitope profiles that suggest functional differences between these two cell types, many of the trophic factors appear to be expressed at similar levels (FIG. 8), which indicates there is some overlap in the trophic functions of MPCs and MSCs. FGF2 and TGFB3 are somewhat general cytokines that promote growth and scarless wound healing, respectively. HGF, LIF and IL10 promote immunosuppression. VEGFA promotes vascular regeneration, and BMP2, BMP4 and BMP6 have been shown to promote bone regeneration.

Figure 9:
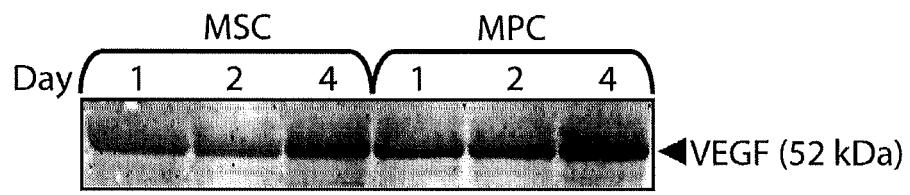
FIG. 9: Protein-level expression of VEGFA in MPCs and MSCs.

The MPCs produced a greater amount of VEGFA at days 1, 2 and 4 than MSCs than MSCs, as observed with western blots (FIG. 9).

Figure 10:
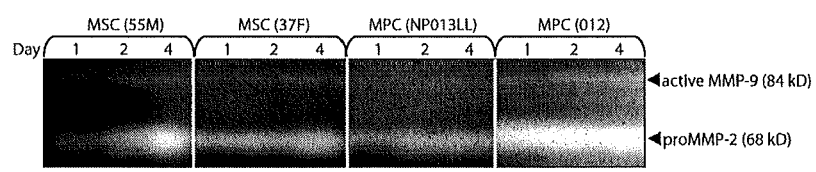
FIG. 10: Protein-level activity of MMPs, via gelatin zymography, in MPCs and MSCs.

MMPs play a role in promoting endothelial cell migration and infiltration. Similar to MSCs, MPCs express MMP-2 and MMP-9. Comparison of the two cell types indicates they express similar levels. However, MPCs begin expressing higher levels of MMP-2 and MMP-9 earlier, i.e. by Day 1 (FIG. 10).

Example 4

Biological Performance of MPCs

A. MPC-Enhanced Axon Growth In Vitro

Figure 11:
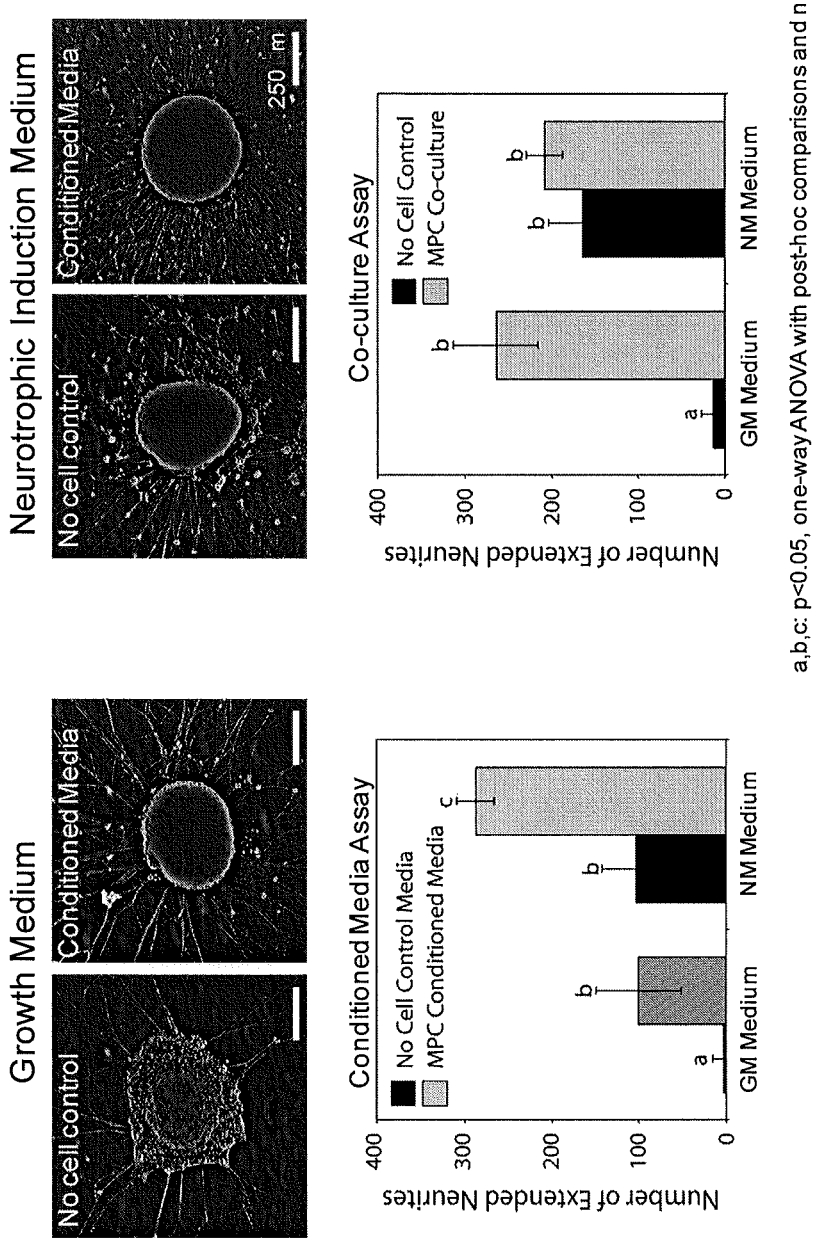
FIG. 11: Illustrates a conditioned media experiment, wherein progenitor cells were cultured in either growth or neurotrophic induction medium. For both media types, medium that was conditioned by the MPCs resulted in a higher density of neurite extensions compared to the corresponding no cell controls.

This experiment was performed in two ways. First, in a conditioned media experiment, we cultured the progenitor cells for three days in either growth or neurotrophic induction medium. Then, we transferred the media to the DRG cultures for an additional three days. For both media types, medium that was conditioned by the MPCs resulted in a higher density of neurite extensions compared to the corresponding no cell controls. FIG. 11. We further quantified this finding by counting the number of extended neurites under each condition and found that the factors secreted by the progenitor cells resulted in a significant increase in the number of neurites that extended beyond the minimum neurite length.

We also performed a co-culture assay, where the progenitor cells were cultured together with the DRGs in a transwell system that allowed soluble factor communication between the two cultures. We found the results of these experiments to be similar to the conditioned media experiment, but one notable difference was that soluble factor communication appeared to enhance the neurotrophic potential of the progenitor cells.

B. MPC Trophic Factor-Induced Endothelial Cell Proliferation

Figure 12:
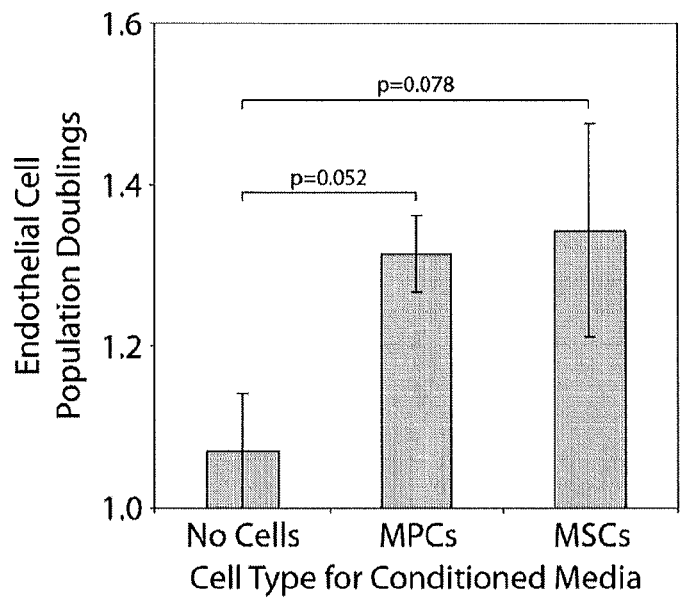
FIG. 12: Endothelial cell proliferation in MPC vs. MSC conditioned media.

MPCs were allowed to secrete their trophic factors into conditioned medium for three days. This medium was then added to fresh media and transferred to endothelial cell culture. Substantial increase in the proliferation of the endothelial cells was observed, as a result of the trophic factors secreted by the MPCs (FIG. 12).

C. MPC Trophic Factor Suppression of Inflammatory Response

Figure 13:
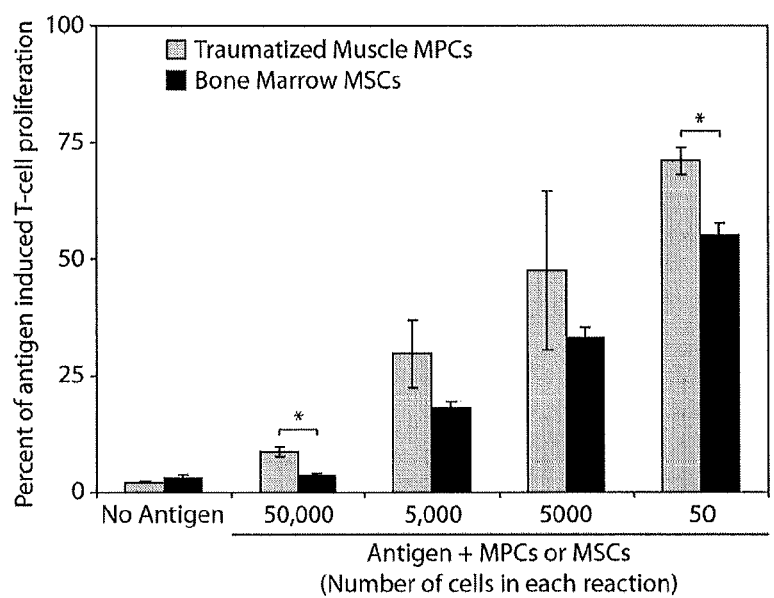
FIG. 13: Suppression of inflammatory response by MPC vs. MSC secreted trophic factors. The data is represented as a percentage of the T-cell proliferation in the positive control sample that was not conditioned by the MPCs factors. Bone marrow MSC Immunosuppression is also represented for comparison.

A mixed lymphocyte reaction was performed to evaluate the immunosuppressive properties of the MPCs. The proliferation to T cells was measured following stimulation with an antigen. The factors secreted by MPCs significantly decreased the T-cell proliferation in a dose-dependent manner (FIG. 13).

Example 5

Peripheral Nerve Graft

A novel, composite electropsun nanofiber scaffold was fabricated and seeded with the MPC cell population to produce a peripheral nerve graft.

Figure 14A:
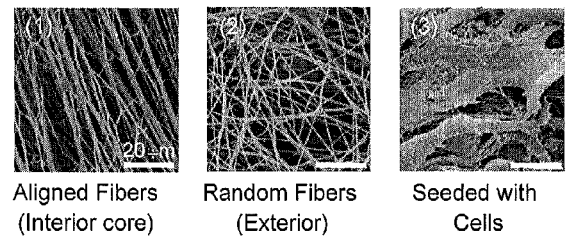
FIG. 14: Peripheral Nerve Graft.

The composite scaffold was fabricated by electrospinning poly(ε)caprolactone into nanometer-scale fibers (FIGS. 1 and 2). There are three important features of the nerve graft: (1) the interior core of the scaffold is filled with aligned nanofibers (FIG. 14a), which are designed to guide axon growth along the interior of the scaffold structure; (2) the aligned fibers of the scaffold are surrounded by a core of non-aligned fibers that support the seeded progenitor cells; and (3) these cells will secrete their neurotrophic factors into the interior core of the scaffold to augment the nerve regeneration process.

Figure 14B:
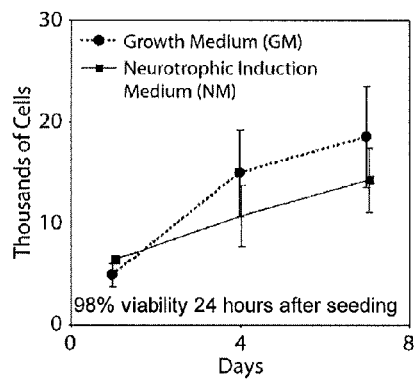
Figure 14C:
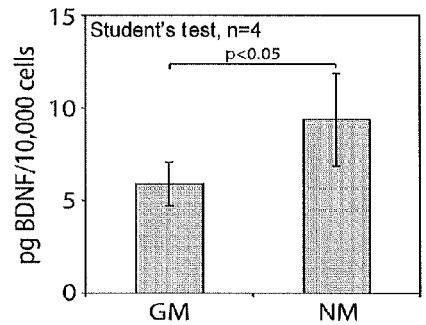
Figure 14D:
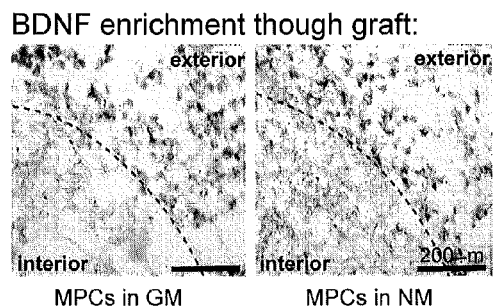

Assays were performed to determine the biological performance of the MPCs in the 3-D environment of the peripheral nerve graft. Viability of the cells in the graft was assessed using a calcein/ethidium bromide fluorescence assay. Within 24 hours, 98% of the seeded cells remained viable and continued to proliferate on the graft at approximately the same rate (FIG. 14b). After one week in culture, the nerve graft was fixed and prepared for immunohistochemical evaluation of the neurotrophic factor distribution in the construct. The seeded cells produced BDNF while in the graft in both growth media and neutrophic induction media, with the MPCs cultured in the neurotrophic induction medium producing more BDNF on a per cell basis (FIG. 14c). FIG. 14d shows cross sections through the graft, with the dotted line indicating the interface between the non-aligned exterior of the graft and the aligned interior core, and with the aligned fibers running in and out of the figure. We found most of the BDNF was localized near the MPCs in the non-aligned region of the graft. In grafts cultured in the neurotrophic induction medium, the secreted factors also enriched the aligned fibers.

The MPCs demonstrated the ability to remain viable and functional after seeding onto the composite nanofibrous scaffold of the peripheral nerve graft. The neurotrophic factors they produced will enhance the neuroconductivity of the aligned nanofibers.

What is claimed is:

1. A graft comprising a scaffold having an injury-facing side and a non-injury-facing side, wherein the scaffold comprises a porous matrix comprising non-aligned fibers, wherein mesenchymal progenitor cells are disposed and retained on the non-injury-facing side, such that, when the graft is applied at a site of injury, the mesenchymal progenitor cells are separated from the injury site by the porous matrix and are in fluid contact with the injury site through the porous matrix, such that, agents produced or secreted by the mesenchymal progenitor cells can diffuse to the injury site.

2. The graft of claim 1, wherein the non-aligned fibers are randomly aligned and form interstices.

3. The graft of claim 2, wherein the fibers have a diameter of about 50-500 nm.

4. The graft of claim 2, wherein the fibers are synthetic fibers.

5. The graft of claim 4, wherein the synthetic fibers are biodegradable polymeric fibers.

6. The graft of claim 1, wherein the porous matrix further comprises additional multiprogenitor cells.

7. The graft of claim 1, wherein the porous matrix further comprises a cell culture medium.

8. The graft of claim 1, wherein the porous matrix further comprises one or more pharmaceutically active agents selected from the group consisting of growth factors, anti-inflammatories, antibiotics, and antivirals.

9. The graft of claim 2, wherein the scaffold further comprises aligned fibers disposed on the injury-facing side of the randomly non-aligned fibers.

10. A graft conduit having an interior surface and an exterior surface, comprising a sheath comprised of a porous matrix comprising non-aligned fibers, wherein mesenchymal progenitor cells are disposed and retained on the exterior surface, such that the mesenchymal progenitor cells are separated from the interior of the conduit by the porous matrix and wherein the mesenchymal progenitor cells are in fluid contact with the interior surface, such that agents produced or secreted by the mesenchymal progenitor cells can diffuse into the interior of the conduit.

11. The graft conduit of claim 10, wherein the non-aligned fibers are randomly aligned and form interstices.

12. The graft conduit of claim 11, further comprising a core comprising aligned fibers interior to the sheath.

13. The graft conduit of claim 12, wherein the aligned fibers are synthetic fibers.

14. The graft conduit of claim 12, wherein the aligned fibers are arranged along an axis of symmetry running longitudinally through the conduit.

15. The graft conduit of claim 12, wherein the aligned fibers and non-aligned fibers are synthetic fibers fabricated from the same material and have a diameter of about 50-500 nm.

16. The graft conduit of claim 15, wherein the fibers are biocompatible and biodegradable.

17. The graft conduit of claim 10, wherein the porous matrix further comprises a cell culture medium.

18. The graft conduit of claim 10, wherein the porous matrix further comprises one or more pharmaceutically active agents selected from the group consisting of growth factors, anti-inflammatories, antibiotics, and antivirals.

19. The graft conduit of claim 10, further comprising a liquid impermeable liner exterior to the sheath.

20. The graft conduit of claim 19, wherein the exterior liner is configured to form a fluid seal with another conduit, creating fluid communication between the interior of the graft conduit and the other conduit and isolating the contents of the graft from external media.

21. The graft conduit of claim 19, wherein the liner comprises a flange extending longitudinally beyond the conduit graft.

22. A method of treating a patient suffering from a tissue injury and in need of tissue restoration and/or regeneration, comprising applying to the injury site a graft having a scaffold having an injury-facing side and a non-injury-facing side, wherein the scaffold comprises a porous matrix comprising non-aligned fibers, wherein mesenchymal progenitor cells are disposed and retained on the non-injury-facing side, such that the mesenchymal progenitor cells are separated from the injury site by the porous matrix and are in fluid contact with the injury site through the porous matrix, such that agents produced or secreted by the mesenchymal progenitor cells can diffuse to the injury site.

23. The method of claim 22, wherein the tissue injury is selected from the group consisting of injury to nerve, bone, and vascular tissue.

24. A method of treating a patient suffering from a tissue injury comprising a gap between a proximal tissue section and a distal tissue section, comprising connecting the proximal tissue section to the distal tissue section with a graft conduit having an interior surface and an exterior surface and comprising a sheath comprised of a porous matrix comprising non-aligned fibers, wherein mesenchymal progenitor cells are disposed and retained on the exterior surface, such that the mesenchymal progenitor cells are separated from the interior of the conduit by the porous matrix and wherein the mesenchymal progenitor cells are in fluid contact with the interior surface, such that agents produced or secreted by the mesenchymal progenitor cells can-diffuse into the interior of the conduit and wherein the graft conduit further comprises a core of aligned fibers interior to the sheath.

25. The method of claim 24, wherein the tissue injury is selected from the group consisting of injury to nerve, bone, and vascular tissue.

26. The method of claim 24, wherein the graft conduit further comprises a liquid impermeable liner exterior to the sheath.

27. The method of claim 26, wherein the exterior liner is configured to form a fluid seal with one or more of the proximal tissue section and the distal tissue section, and wherein the connecting includes creating a fluid communication between the interior of the graft conduit and one or more of the proximal tissue section and the distal tissue section and isolating the contents of the graft from external media.

* * * * *

UNITED STATES PATENT AND TRADEMARK OFFICE
CERTIFICATE OF CORRECTION

PATENT NO.        : 8,652,458 B2                           Page 1 of 1
APPLICATION NO.   : 13/129636
DATED             : February 18, 2014
INVENTOR(S)       : Wesley M. Jackson et al.

It is certified that error appears in the above-identified patent and that said Letters Patent is hereby corrected as shown below:

ON THE TITLE PAGE:

Correct item (73) Assignees, as follows:

Delete "The United States of America, as represented by the Secretary of the Army, U.S.A., Washington, DC" and insert -- The Government of the United States, as represented by the Secretary of the Army, U.S.A., Fort Detrick, Maryland --.

Delete "The United States of America, as represented by the Secretary of the Department of Health and Human Services, Washington, DC" and insert -- The Government of the United States, as represented by the Secretary of the Department of Health and Human Services, Rockville, Maryland --.

Signed and Sealed this
Twenty-fourth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,652,458 B2  
APPLICATION NO. : 13/129636  
DATED            : February 18, 2014  
INVENTOR(S)      : Jackson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this

Twenty-ninth Day of September, 2015

Michelle K. Lee  
*Director of the United States Patent and Trademark Office*